(12) United States Patent
Hu et al.

(10) Patent No.: US 6,809,119 B2
(45) Date of Patent: Oct. 26, 2004

(54) BRANCHED CHAIN AMINO ACID-DEPENDENT AMINOTRANSFERASE INHIBITORS AND THEIR USE IN THE TREATMENT OF NEURODEGENERATIVE DISEASES

(75) Inventors: Lain-Yen Hu, Ann Arbor, MI (US); Suzanne Ross Kesten, Ann Arbor, MI (US); Huangshu Lei, Ann Arbor, MI (US); Todd Robert Ryder, Rochester, NY (US); David Juergen Wustrow, Ann Arbor, MI (US)

(73) Assignee: Warner-Lambert Company LLC, Ann Arbor, MI (US)

( * ) Notice: Subject to any disclaimer, the term of this patent is extended or adjusted under 35 U.S.C. 154(b) by 0 days.

(21) Appl. No.: 10/304,803

(22) Filed: Nov. 26, 2002

(65) Prior Publication Data

US 2003/0149110 A1 Aug. 7, 2003

Related U.S. Application Data

(60) Provisional application No. 60/333,636, filed on Nov. 27, 2001.

(51) Int. Cl.$^7$ .................. A61K 31/18; C07C 311/49
(52) U.S. Cl. .................. 514/604; 514/602; 514/603; 564/81; 564/430
(58) Field of Search .................. 564/81, 430; 514/602, 514/604, 562, 603

(56) References Cited

FOREIGN PATENT DOCUMENTS

| EP | 0811375 | 12/1997 |
|----|---------|---------|
| EP | 1044970 | 10/2000 |
| WO | 0142191 | 6/2001 |
| WO | 0224672 | 3/2002 |
| WO | 0244126 | 6/2002 |

OTHER PUBLICATIONS

Pekhtereva et al. Chem. Abst. 113:77558 (1990).*
Bellesia et al. Chem. Abst. 97:181890 (1982).*
Dudman et al. Chem. Abst. 94:156465 (1981).*
Shirai et al. Chem. Abst. 52:34994 (1958).*
Tisdell et al. CA 132:308343 (2000).*
Shah et al. CA 126:7955 (1996).*
Strupczewski et al. CA 114:62120 (1991).*
Shevchenko et al. CA 90:6057 (1979).*
Anderson et al. CA 84:43882 (1976).*
White et al. CA 66:104845 (1967).*
Shirai et al. CA 52:34994 (1958).*
Bennett et al. CA 44:56328 (1950).*
Enany et al. CA 77:139,552 (1972).*
Ito et al. CA 85:21237 (1976).*
Chernykh CA 87:133624 (1977).*
PCT International Search Report, PCT/IB02/04386.
Pekhtereva, T. M. et al, "The effect of N–substituents on the chemical shifts and spin–spin couplin constants of the HNNH group in benzenesulfonylhydrazine derivatives", *Ukrainskii Khimicheskii Zhurnal,* (1990), vol. 56(2), pp. 186–190.
Enany, M. M. et al, "Certain arylsulfonyl derivatives of [(arenesulfonamido) benzyl] hydrazines", *United Arab Republic Journal of Pharmaceutical Sciences,* (1971), vol. 12(1), pp. 17–23.
Ariesan, V. et al, "Acylsulfonhydrazines with antitrichomonal activity", *Farmacia,* (1971), vol. 19(4), pp. 213–218.
Kagthara, Preeti R., et al, "Synthesis of some arylamides, sulfonamides and 5–oxoimidazolines as novel bioactive compounds derived from benzimidazole", *Heterocyclic Communications,* (1998), vol. 4(6), pp. 561–566.
Bux M. et al, "Synthesis of 3–methoxy–4–allyloxybenzohydrazide and its hydrazones as potential fungicides" *Vijnana Parishad Anusandhan Patrika,* (1987), vol. 30(4), pp. 21–17.
Beilstein Registry No. 3422626.
Beilstein Registry No. 3432018.
Ariesan, V. et al, "Synthesis of acylsulfonylhydrazine derivatives", *Archiv der Pharmazie und Berichte der Deutschen Pharmazeutischen Gesellschaft,* (1992), vol. 305(3), pp. 199–208.
Reinecke, Manfred G. et al, "Another rearrangement during the photolysis of lithium 3–[(p–tolylsulfonyl)amino]–1,2, 3–benzotriazin–4(3H)–one", *Journal of Organic Chem,* (1998), vol. 53 (1), pp. 208–210.
Chernova, N. I. et al, "5–Methoxy–2–p–(tosylamino) benzaldehyde", *Metody Poluch. Khim. Reaktiv Prep.,* (1971), No. 23, pp. 123–125.

* cited by examiner

Primary Examiner—Peter O'Sullivan
(74) Attorney, Agent, or Firm—Scully, Scott, Murphy & Presser

(57) ABSTRACT

The invention relates to BCAT inhibitors and the use thereof for treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the overstimulation of the excitatory amino acids, treating anxiety, psychosis, convulsions, aminoglycoside antibiotics-induced hearing loss, migraine headache, chronic pain, neuropathic pain, Parkinson's disease, diabetic retinopathy, glaucoma, CMV retinitis, urinary incontinence, opioid tolerance or withdrawal, and inducing anesthesia, as well as for enhancing cognition.

7 Claims, No Drawings

BRANCHED CHAIN AMINO ACID-DEPENDENT AMINOTRANSFERASE INHIBITORS AND THEIR USE IN THE TREATMENT OF NEURODEGENERATIVE DISEASES

This application claims benefit of U.S. Provisional Application No. 60/333,636 filed Nov. 27, 2001.

FIELD OF THE INVENTION

This invention is related to branched chain amino acid-dependent amino transferase (BCAT) inhibitors. The invention is also directed to the use of BCAT inhibitors as neuro-protective agents for treating conditions such as stroke, cerebral ischemia, central nervous system trauma, hypoglycemia, anxiety, convulsions, aminoglycoside antibiotics-induced hearing loss, migraine headaches, chronic pain, neuropathic pain, glaucoma, CMV retinitis, diabetic retinopathy, psychosis, urinary incontinence, opioid tolerance or withdrawal, or neuro-degenerative disorders such as lathyrism, Alzheimer's disease, Parkinsonism, amyotrophic lateral sclerosis (ALS), and Huntington's Disease.

RELATED BACKGROUND ART

Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-aspartate (NMDA) receptor. This excitotoxic action is considered responsible for the loss of neurons in cerebrovascular disorders such as cerebral ischemia or cerebral infarction resulting from a range of conditions, such as thromboembolic or hemorrhagic stroke, cerebral vasospasms, hypoglycemia, cardiac arrest, status epilepticus, perinatal asphyxia, anoxia such as from drowning, pulmonary surgery and cerebral trauma, as well as lathyrism, Alzheimer's disease, Parkinson's disease, and Huntington's disease.

Excitatory amino acid receptor antagonists that block NMDA receptors are recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain and anxiety, and may be a significant causal factor in chronic neurodegenerative disorders such as Parkinson's disease (Klockgether T., Turski L., *Ann. Neurol.*, 1993;34:585–593), human immunodeficiency virus (HIV) related neuronal injury, amyotrophic lateral sclerosis (ALS), Alzheimer's disease (Francis P. T., Sims N. R., Procter A. W., Bowen D. M., *J. Neurochem.*, 1993;60(5):1589–1604, and Huntington's disease (see Lipton S., *TINS*, 1993;16(12):527–532; Lipton S. A., Rosenberg P. A., *New Eng. J. Med.*, 1994;330(9):613–622; and Bigge C. F., *Biochem Pharmacol*, 1993;45:1547–1561, and referenced cited therein). NMDA receptor antagonists may also be used to prevent tolerance to opiate analgesia or to help control withdrawal symptoms from addictive drugs (Eur. Pat. Appl. 488,959A).

U.S. Pat. No. 5,352,683 discloses the treatment of chronic pain with a compound which is an antagonist of the NMDA receptor.

U.S. Pat. No. 4,902,695 discloses certain competitive NMDA antagonists that are useful for the treatment of neurological disorders, including epilepsy, stroke, anxiety, cerebral ischemia, muscular spasms, and neurodegenerative diseases such as Alzheimer's disease and Huntington's disease.

U.S. Pat. No. 5,192,751 discloses a method of treating urinary incontinence in a mammal which comprises administering an effective amount of a competitive NMDA antagonist.

SUMMARY OF THE INVENTION

The invention relates BCAT inhibitor compounds of Formula I

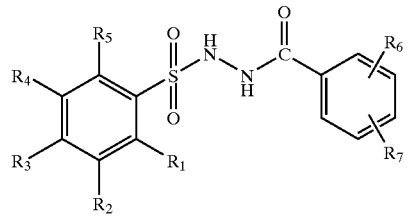

wherein:

$R_3$ is H, halogen, alkyl, carboxy, alkoxy, substituted alkoxy; $R_1$, $R_2$, $R_4$ and $R_5$ are independently, H, alkyl, substituted alkyl, alkoxy, substituted alkoxy, $NO_2$, halogen, or $CF_3$;

$R_6$ or $R_7$ are independently, H, halogen, alkyl, substituted alkyl, arylalkyl, substituted arylalkyl, $C(CH_2)_n$—$NHSO_2$-aryl, $C(CH_2)_n$—$NHSO_2$-substituted aryl, $(CH_2)_n$—$NHSO_2$-alkyl, $(CH_2)_n$—$NHSO_2$-substituted alkyl, $(CH_2)_n$—$NHSO_2$-arylalkyl, $(CH_2)_n$—$NHSO_2$-substituted arylalkyl, $NHSO_2$-aryl, $NHSO_2$-substituted aryl, $NHSO_2$-alkyl, $NHSO_2$-substituted alkyl, $NHSO_2$-arylalkyl, $NHSO_2$-substituted arylalkyl, $(CH_2)_n$-aryl, $(CH_2)_n$-substituted aryl, $(CH_2)_n$-alkyl, $(CH_2)_n$-substituted alkyl, O-aryl, O-substituted aryl, O-alkyl, O-substituted alkyl, O-arylalkyl, O-substituted arylalkyl, $(CH_2)_n$—$SO_2NH$-aryl, $(CH_2)_n$—$SO_2NH$-substituted aryl, $(CH_2)_n$—$SO_2NH$-alkyl, $(CH_2)_n$—$SO_2NH$-substituted alkyl, $(CH_2)_n$—$C(O)NH$-arylalkyl, $(CH_2)_n$—$C(O)NH$-substituted arylalkyl, $(CH_2)_n$—$C(O)NH$-aryl, $(CH_2)_n$—$C(O)NH$-substituted aryl, $(CH_2)_n$—$C(O)NH$-alkyl, $(CH_2)_n$—$C(O)NH$-substituted alkyl, $(CH_2)_n$—$SO_2NH$-arylalkyl, $(CH_2)_n$—$SO_2NH$-substituted arylalkyl, $(CH_2)_n$—$NH_2$, $(CH_2)_n$—$NH$-aryl, $(CH_2)_n$—$NH$-substituted aryl, $(CH_2)_n$—$NH$-alkyl, $(CH_2)_n$—$NH$-substituted alkyl, $(CH_2)_n$—$NH$-arylalkyl, $(CH_2)_n$—$NH$-substituted arylalkyl, $(CH_2)_n$—$NHSO_2$-aryl, $(CH_2)_n$—$NHSO_2$-substituted aryl, $(CH_2)_n$—$NHSO_2$-alkyl, $(CH_2)_n$—$NHSO_2$-substituted alkyl, $(CH_2)_n$—$NHC(O)$-arylalkyl, $(CH_2)_n$—$NHC(O)$-substituted arylalkyl, $(CH_2)_n$—$NO_2$, (C≡C)-alkyl. (C≡C)-substituted alkyl, (C≡C)-arylalkyl, (C≡C)-substituted arylalkyl, (C≡C)-aryl, or (C≡C)-substituted aryl; and n is 0, 1, 2, or 3.

or a pharmaceutically acceptable salt, ester, prodrug, or amide thereof;

where there is more than one stereoisomer, each chiral center may be independently R or S; or a pharmaceutically acceptable salt, ester, prodrug, or amide thereof;

The invention also relates to compounds of Formula I, wherein $R_1$, $R_2$, $R_3$, $R_4$, and $R_5$ are hydrogen; and $R_6$ or $R_7$ is —$NHSO_2$-aryl, —$NHSO_2$-substituted aryl, —$NHSO_2$-alkyl, or —$NHSO_2$-substituted alkyl.

The invention also relates to compounds selected from:

Benzoic acid, 4-nitro-2-(phenylsulfonyl)hydrazide;
Benzoic acid, 4-amino-2-(phenylsulfonyl)hydrazide;
Benzoic acid, 4-[[(2,4,6-trichlorophenyl)sulfonyl]amino]-, 2-(phenylsulfonyl)hydrazide;
Benzoic acid, 4-[[[4-(trifluoromethyl)phenyl]sulfonyl]amino]-, 2-(phenylsulfonyl)hydrazide;
Benzoic acid, 4-[[(3,4-dimethoxyphenyl)sulfonyl]amino]-, 2-(phenylsulfonyl)hydrazide;
Benzoic acid, 4-[[[(4-phenoxy)benzene]sulfonyl]amino]-, 2-(phenylsulfonyl)hydrazide;
Benzoic acid, 4-[[(2-chloro-6methylphenyl)sulfonyl]amino]-, 2-(phenylsulfonyl)hydrazide;
Benzoic acid, 4-[(methylsulfonyl)amino]-, 2-(phenylsulfonyl)hydrazide;
Benzoic acid, 4-[[(4-methylphenyl)sulfonyl]amino]-, 2-(phenylsulfonyl)hydrazide;
Benzoic acid, 4-[[(4-ethylphenyl)sulfonyl]amino]-, 2-(phenylsulfonyl)hydrazide;
Benzoic acid, 4-[[(4-n-propylphenyl)sulfonyl]amino]-, 2-(phenylsulfonyl)hydrazide;
Benzoic acid, 4-[[(4-n-butylphenyl)sulfonyl]amino]-, 2-(phenylsulfonyl)hydrazide;
Benzoic acid, 4-[[(4-n-pentylphenyl)sulfonyl]amino]-, 2-(phenylsulfonyl)hydrazide;
Benzoic acid, 4-[[(4-fluorophenyl)sulfonyl]amino]-, 2-(phenylsulfonyl)hydrazide;
Benzoic acid, 4-[phenylsulfonyl]amino]-, 2-(phenylsulfonyl)hydrazide;
4-Benzylamino-benzoic acid 2-(phenylsulfonyl)hydrazide;
Benzoic acid, 4-[[(3-methylphenyl)sulfonyl]amino]-, 2-(phenylsulfonyl)hydrazide;
4-Phenoxybenzoic acid, 2-[(3-methyl)phenylsulfonyl]hydrazide;
4-Phenoxybenzoic acid, 2-[3-bromophenylsulfonyl]hydrazide;
4-Phenoxybenzoic acid, 2-[2-chlorophenylsulfonyl]hydrazide;
4-Phenoxybenzoic acid, 2-[2-(trifluoromethoxy)phenylsulfonyl]hydrazide;
4-Phenoxybenzoic acid, 2-[(4-methyl-3-nitro)phenylsulfonyl]hydrazide;
4-Phenoxybenzoic acid, 2-[2-trifluorophenylsulfonyl]hydrazide;
4-(1,1-Dimethylethyl)-benzoic acid 2-(phenylsulfonyl)hydrazide;
[1,1'-Biphenyl]-4-carboxylic acid 2-(phenylsulfonyl)hydrazide;
3-Phenoxybenzoic acid, 2-(phenylsulfonyl)hydrazide;
2-Phenoxybenzoic acid, 2-(phenylsulfonyl)hydrazide;
4-Phenoxybenzoic acid, 2-(phenylsulfonyl)hydrazide;
4-Benzyloxybenzoic acid, 2-(phenylsulfonyl)hydrazide;
Benzoic acid, 4-[[(4-methoxyphenyl)sulfonyl]amino]-, 2-(phenylsulfonyl)hydrazide;
4-Iodo-benzoic acid, 2-(phenylsulfonyl)hydrazide;
4-Phenacetylenyl-benzoic acid, 2-(phenylsulfonyl)hydrazide;
Phenethyl-benzoic acid, 2-(phenylsulfonyl)hydrazide;
4-(3-Cyclohexyl-1-propynyl)-benzoic acid, 2-(phenylsulfonyl)hydrazide;
4-(3-Cyclohexyl-3-hydroxy-1-propynyl)-benzoic acid, 2-(phenylsulfonyl)hydrazide;
4-(3-Cyclohexyl-3-hydroxy-1-propyl)-benzoic acid, 2-(phenylsulfonyl)hydrazide;
4-(3,3-Dimethyl-1-butynyl)-benzoic acid, 2-(phenylsulfonyl)hydrazide; and
4-(3,3-Dimethyl-1-butyl)-benzoic acid, 2-(phenylsulfonyl)hydrazide.

The invention also relates to a method of treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease, Parkinson's disease and Down's syndrome, treating or preventing the adverse consequences of the overstimulation of the excitatory amino acids, treating anxiety, psychosis, convulsions, chronic pain, neuropathic pain, diabetic retinopathy, glaucoma, CMV retinitis, urinary incontinence, and inducing anesthesia, as well as enhancing cognition, and preventing opiate tolerance and withdrawal symptoms, comprising administering to an animal in need of such treatment an effective amount of any one of the BCAT inhibitors of the present invention, or a pharmaceutically acceptable salt thereof.

The present invention also includes a pharmaceutical composition comprising a therapeutically effective amount of one or more compounds of Formula I and a pharmaceutically acceptable carrier.

DETAILED DESCRIPTION OF THE INVENTION

The present invention is predicated on the discovery that intraocular glutamate injection causes ganglion cell loss which is related to the early stages of diabetic retinopathy (Vorwerk et al., *IOVS,* 1996;37:1618–1624) and that an inhibitor of the branched chain amino acid-dependent aminotransferase pathway, specifically gabapentin, is effective in inhibiting the synthesis of glutamate (see example below), thus preventing diabetic retinopathy. Accordingly, the present invention provides a method for the prophylactic and therapeutic treatment of diabetic retinopathy, including treatment at the pre-diabetic retinopathy stage, the nonproliferative diabetic retinopathy stage, and the proliferative diabetic retinopathy stage. By "prophylactic" is meant the protection, in whole or in part, against diabetic retinopathy, in particular diabetic macular edema. By "therapeutic" is meant the amelioration of diabetic retinopathy, itself, and the protection, in whole or in part, against further diabetic retinopathy, in particular diabetic macular edema.

The method comprises the administration of an inhibitor of the branched chain amino acid-dependent aminotransferase pathway in an amount sufficient to treat the neurodegenerative disease or condition, for example, to treat the retina for retinopathy prophylactically or therapeutically. Any inhibitor of the branched chain amino acid-dependent aminotransferase pathway can be used in the method of the present invention as long as it is safe and efficacious. Herein, "branch chain amino acid-dependent aminotransferase (BCAT) inhibitor" will be used to refer to such compounds and is intended to encompass all compounds that affect the branch chain amino acid-dependent aminotransferase pathway at any and all points in the pathway.

Preferably, the BCAT inhibitor is a compound of Formula I as described above, or a pharmaceutically acceptable, BCAT pathway-inhibiting analogue or prodrug thereof or a pharmaceutically acceptable salt, ester, or amide of any of the foregoing.

Unless otherwise expressly stated, the following definitions are adhered to throughout this disclosure.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc), cycloalkyl (alicyclic) groups (e.g., cyclopropyl, cyclopentyl, cyclohexyl, cycloheptyl, cyclooctyl), alkyl substituted cycloalkyl groups, and cycloalkyl substituted alkyl groups. The term "alkyl" further includes alkyl groups, which can further include oxygen, nitrogen, sulfur, or phosphorous atoms replacing one or more carbons of the hydrocarbon backbone. These heteroatoms can also be substituted. For example, sulfur may be substituted with one or more oxygen atoms (e.g., SO or $SO_2$). In certain embodiments, a straight-chain or branched-chain alkyl has 6 or fewer carbon atoms in its backbone (e.g., $C_1$–$C_6$ for straight chain, $C_3$–$C_6$ for branched chain), and more preferably 4 or fewer. Likewise, preferred cycloalkyls have from 3 to 8 carbon atoms in their ring structure, and more preferably have 5 or 6 carbons in the ring structure. The term $C_1$–$C_6$ includes alkyl groups containing 1 to 6 carbon atoms.

Moreover, the term "alkyl" includes both "unsubstituted alkyls" and "substituted alkyls," the latter of which refers to alkyl moieties having substituents replacing a hydrogen on one or more carbons of the hydrocarbon backbone.

The term "alkyl" also includes the side chains of natural and unnatural amino acids. In an embodiment, the term "cycloalkyl" includes saturated hydrocarbon rings having 3 to 8 carbon atoms and further includes, for example, cyclopropyl, cyclobutyl, cyclopentyl, cyclohexyl, cycloheptyl, cyclooctyl, and the like.

Unless the number of carbons is otherwise specified, "lower alkyl" as used herein means an alkyl group, as defined above, but having from 1 to 5 carbon atoms in its backbone structure. In an embodiment, the term "lower alkyl" includes straight or branched hydrocarbon radicals having from 1 to 4 carbon atoms and includes, for example, methyl, ethyl, n-propyl, isopropyl, n-butyl, sec-butyl, isobutyl, or tert-butyl. "Lower alkenyl" and "lower alkynyl" have chain lengths of, for example, 2 to 5 carbon atoms.

The term "substituted" includes substitution by one or more substituents selected from, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, aryloxy, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl, and ureido), amidino, imino, sulfhydryl, alkylthio, arylthio, thiocarboxylate, sulfate, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl [e.g., phenylmethyl (benzyl)].

The term "aryl" includes groups, including 5- and 6-membered single-ring aromatic groups that may include from 0 to 4 heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heterocycles," "heteroaryls," or "heteroaromatics". The aromatic ring can be substituted at one or more ring positions with such substituents as described above, as for example, halogen, hydroxyl, alkoxy, aryloxy, alkylcarbonyloxy, arylcarbonyloxy, alkoxycarbonyloxy, aryloxycarbonyloxy, carboxylate, alkylcarbonyl, alkylaminocarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl, and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin). In an embodiment, the heteroaromatic group is 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, or 2-, 3-, 4-, 5-, 6-, or 7-indolyl.

Other examples of heterocycles include 5- or 6-membered mono- or bicyclic ring structures which may contain one or more heteroatoms such as N, S, or O; examples of heterocycles are pyridine, pyrimidine, pyridazine, pyrazole, oxazole, indole, N-alkylindole, quinoline, quinazoline, quinazolinone, and the like. Substituents may include substituted or unsubstituted lower alkyl, substituted or unsubstituted alkenyl, substituted or unsubstituted alkynyl, substituted or unsubstituted araalkyl, substituted or unsubstituted aryl, halogen, cyano, nitro, CHO, $COR_8$, $OR_8$, $COOR_8$, $CONR_8R_9$, $(CH_2)_nNR_8R_9$, $(CH_2)_nOR_8$, $SR_8$, $SOR_8$, $SO_2R_8$, $NHSO_2R_8$, $NR_8R_9$, $NHCOR_8$, $O(CR_8R_9)_{0-3}$ $CF_3$, $O(R_8R_9)_{0-3}CCl_3$, or $SO_2NR_8R_9$, $SCF_3$, $SCCl_3$, wherein $R_8$ and $R_9$ are independently hydrogen, substituted or unsubstituted lower alkyl, substituted or unsubstituted lower alkenyl, substituted or unsubstituted alkynyl, substituted or unsubstituted araalkyl.

The term "phenyl" includes aromatic rings of 6 carbons. Phenyl may be unsubstituted (or substituted with hydrogen) or substituted at one or more positions with a substituent such as, but not limited to, alkyl, alkenyl, alkynyl, halogen, hydroxyl alkoxy, aryloxy, alkylcarbonyloxy, arylcarbonyloxy, alkoxycarbonyloxy, aryloxycarbonyloxy, carboxylate, alkylcarbonyl, alkylaminocarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano. amino (including alkyl amino, dialkylamino, arylamino, diarylamino, and alkylarylamino), acylamino (including alkylcarbonylamino, arylcarbonylamino, carbamoyl, and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. The term "aryl" is intended to include both substituted and unsubstituted phenyl groups.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl, and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl, and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl," "alkylaminoalkyl," and "thioalkoxyalkyl" include alkyl groups, as described above, which further include oxygen, nitrogen, or sulfur atoms replacing one or more carbons of the hydrocarbon backbone, e.g., oxygen, nitrogen, or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl, and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc. In an embodiment, the term "lower alkoxy" includes O-alkyl, wherein alkyl is as defined above for lower alkyl.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to, alkthioalkyls, alkthioalkenyls, and alkthioalkynyls. The term "alkthioalkyls" includes compounds with an alkyl, alkenyl, or alkynyl group bonded to a sulfur atom which is bonded to an alkyl group. Similarly, the terms "alkthioalkenyls" and "alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O—. The term "halogen" includes fluorine, bromine, chlorine, iodine, etc. The term "perhalogenated" generally refers to a moiety wherein all hydrogens are replaced by halogen atoms.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

The term "arenes" means a hydrocarbon including an aryl group.

The term "subject" includes organisms which are capable of having or have a chemokine mediated disorder. Preferred examples include humans and animals, including cows, sheep, pigs, dogs, cats, rats, ferrets, bears, rabbits, etc.

The term "treatment" includes the diminishment or alleviation of at least one symptom associated or caused by the disorder being treated. For example, treatment can be diminishment of several symptoms of a disorder or complete eradication of a disorder.

The symbol "—" means a bond.

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of Formula I are capable of further forming both pharmaceutically acceptable formulations comprising salts, esters, amides, and prodrugs. As used herein, the term "pharmaceutically acceptable salts, esters, amides, and prodrugs" refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed and including, but not limited to, acid addition and/or base salts, solvents and N-oxides of a compound of Formula I. This invention also provides pharmaceutical formulations comprising a compound of Formula I together with a pharmaceutically acceptable carrier, diluent, or excipient therefor. All of these forms are within the present invention.

Pharmaceutically acceptable acid addition salts of the compounds of Formula I include salts derived form inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge, et al., "Pharmaceutical Salts," *J. of Pharmaceutical Science*, 1977;66:1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge et al., supra., 1977 both of which are incorporated herein by reference.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines, and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above Formulae, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987 (incorporated herein by reference. In general, a prodrug is a drug which has been chemically modified and may be biologically inactive at its site of action, but which may be degraded or modified by one or more enzymatic or other in vivo processes to the parent bioactive form.

A "therapeutically effective amount" is an amount of a compound of Formula I that when administered to a patient, ameliorates a symptom of the disease.

The BCAT inhibitor, which is preferably a compound of Formula I, a BCAT pathway-inhibiting analogue of Formula I, a BCAT pathway-inhibiting prodrug of Formula I, or a pharmaceutically acceptable salt of any of the foregoing, can be administered in accordance with the present inventive method by any suitable route. Suitable routes of administration include systemic, such as orally or by injection, topical, intraocular, periocular (e.g., subTenon's), subconjunctival, subretinal, suprachoroidal and retrobulbar. The manner in which the BCAT inhibitor is administered is dependent, in part, upon whether the treatment of retinopathy is prophylactic or therapeutic. The manner in which the BCAT inhibitor is administered for therapeutic treatment of retinopathy is dependent, in part, upon the cause of the retinopathy.

For example, given that diabetes is the leading cause of retinopathy, the BCAT inhibitor can be administered prophylactically as soon as the pre-diabetic retinopathy state is detected. For the prophylactic treatment of retinopathy that can result from diabetes, the BCAT inhibitor is preferably administered systemically, e.g., orally or by injection. For the therapeutic treatment of nonproliferative diabetic retinopathy, the BCAT inhibitor can be administered systemically, e.g., orally or by injection, or intraocularly. Proliferative diabetic retinopathy can be therapeutically treated by the administration of the BCAT inhibitor intraocularly, topically, subconjunctivally or periocularly (e.g., subTenon's), for example. The BCAT inhibitor is preferably administered intraocularly, topically, subconjunctivally or periocularly (e.g., subTenon's) for the prophylactic or therapeutic treatment of retinopathy before, during or after surgical removal from an eye of scar tissue generated during neovascularization during the proliferative diabetic stage.

The BCAT inhibitor is preferably administered as soon as possible after it has been determined that an animal, such as a mammal, specifically a human, is at risk for retinopathy (prophylactic treatment) or has begun to develop retinopathy (therapeutic treatment). Treatment will depend, in part, upon the particular BCAT inhibitor used, the amount of the BCAT inhibitor administered, the route of administration, and the cause and extent, if any, of retinopathy realized.

One skilled in the art will appreciate that suitable methods of administering a BCAT inhibitor, which is useful in the present inventive methods, are available. Although more than one route can be used to administer a particular BCAT inhibitor, a particular route can provide a more immediate and more effective reaction than another route. Accordingly, the described routes of administration are merely exemplary and are in no way limiting.

The dose administered to an animal, particularly a human, in accordance with the present invention should be sufficient to effect the desired response in the animal over a reasonable time frame. One skilled in the art will recognize that dosage will depend upon a variety of factors, including the strength of the particular BCAT inhibitor employed, the age, species, condition or disease state, and body weight of the animal, as well as the amount of the retina about to be affected or actually affected by retinopathy. The size of the dose also will be determined by the route, timing and frequency of administration as well as the existence, nature, and extent of any adverse side effects that might accompany the administration of a particular BCAT inhibitor and the desired physiological effect. It will be appreciated by one of ordinary skill in the art that various conditions or disease states, in particular, chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. The present inventive method will typically involve the administration of from about 1 mg/kg/day to about 100 mg/kg/day, preferably from about 15 mg/kg/day to about 50 mg/kg/day, if administered systemically. Intraocular administration typically will involve the administration of from about 0.1 mg total to about 5 mg total, preferably from about 0.5 mg total to about 1 mg total. A preferred concentration for topical administration is 100 mu M.

Compositions for use in the present inventive method preferably comprise a pharmaceutically acceptable carrier and an amount of a BCAT inhibitor sufficient to treat retinopathy prophylactically or therapeutically. The carrier can be any of those conventionally used and is limited only by chemico-physical considerations, such as solubility and lack of reactivity with the compound, and by the route of administration. It will be appreciated by one of ordinary skill in the art that, in addition to the following described pharmaceutical compositions, the BCAT inhibitor can be formulated as polymeric compositions, inclusion complexes, such as cyclodextrin inclusion complexes, liposomes, microspheres, microcapsules and the like (see, e.g., U.S. Pat. Nos. 4,997,652; 5,185,152; and 5,718,922).

The BCAT inhibitor can be formulated as a pharmaceutically acceptable acid addition salt. Examples of pharmaceutically acceptable acid addition salts for use in the pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulphonic, for example p-toluenesulphonic, acids.

The pharmaceutically acceptable excipients described herein, for example, vehicles, adjuvants, carriers or diluents, are well-known to those who are skilled in the art and are readily available to the public. It is preferred that the pharmaceutically acceptable carrier be one which is chemically inert to the BCAT inhibitor and one which has no detrimental side effects or toxicity under the conditions of use.

The choice of excipient will be determined in part by the particular BCAT inhibitor, as well as by the particular method used to administer the composition. Accordingly, there is a wide variety of suitable formulations of the pharmaceutical composition of the present invention. The following formulations are merely exemplary and are in no way limiting.

Injectable formulations are among those that are preferred in accordance with the present inventive method. The requirements for effective pharmaceutically carriers for injectable compositions are well-known to those of ordinary skill in the art (see Pharmaceutics and Pharmacy Practice, J. B. Lippincott Co., Philadelphia, Pa., Banker and Chalmers, eds., pages 238–250 (1982), and ASHP Handbook on Injectable Drugs, Toissel, 4th ed., pages 622–630 (1986). It is preferred that such injectable compositions be administered intramuscularly, intravenously, or intraperitoneally.

Topical formulations are well-known to those of skill in the art. Such formulations are suitable in the context of the present invention for application to the skin. The use of patches, corneal shields (see, e.g., U.S. Pat. No. 5,185,152), and ophthalmic solutions (see, e.g., U.S. Pat. No. 5,710,182) and ointments, e.g., eye drops, is also within the skill in the art.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The effectiveness of an orally administered drug is dependent upon the drug's efficient transport across the mucosal epithelium and its stability in entero-hepatic circulation. Drugs that are effective after parenteral administration but less effective orally, or whose plasma half-life is considered too short, may be chemically modified into a prodrug form.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inhibitor can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride, with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants. Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metals, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-p-aminopropionates, and 2-alkyl-imidazoline quaternary ammonium salts, and (e) mixtures thereof.

The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17.

The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Such compositions can be formulated as intraocular formulations, sustained-release formulations or devices (see, e.g., U.S. Pat. No. 5,378,475). For example, gelantin, chondroitin sulfate, a polyphosphoester, such as bis-2-hydroxyethyl-terephthalate (BHET), or a polylactic-glycolic acid (in various proportions) can be used to formulate sustained-release formulations. Implants (see, e.g., U.S. Pat. Nos. 5,443,505; 4,853,224; and 4,997,652), devices (see, e.g., U.S. Pat. Nos. 5,554,187; 4,863,457; 5,098,443; and 5,725,493), such as an implantable device, e.g., a mechanical reservoir, an intraocular device or an extraocular device with an intraocular conduit (e.g., 100 mu–1 mm in diameter), or an implant or a device comprised of a polymeric composition as described above, can be used.

The present inventive method also can involve the co-administration of other pharmaceutically active compounds. By "co-administration" is meant administration before, concurrently with, e.g., in combination with the BCAT inhibitor in the same formulation or in separate formulations, or after administration of a BCAT inhibitor as described above. For example, corticosteroids, e.g., prednisone, methylprednisolone, dexamethasone, or triamcinalone acetinide, or noncorticosteroid anti-inflammatory compounds, such as ibuprofen or flubiproben, can be co-administered. Similarly, vitamins and minerals, e.g., zinc, antioxidants, e.g., carotenoids (such as a xanthophyll carotenoid like zeaxanthin or lutein), and micronutrients can be co-administered. A general synthetic scheme for preparing compounds of Formula I is set forth below.

Scheme 1

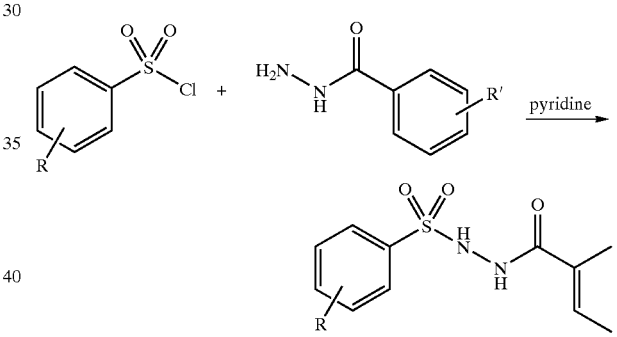

EXAMPLE 1

Benzoic acid, 4-nitro-2-(phenylsulfonyl)hydrazide

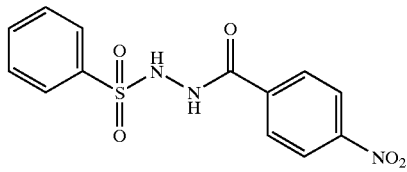

A solution of 4-nitro benzoic acid (0.2 g, 1.2 mmol in 10 mL of dry THF) was cooled to 0° C., treated with N-methylmorpholine (1.6 mL, 14.6 mmol) as well as isobutylchloroformate (1.7 mL, 1.3 mmol), and stirred for 10 minutes prior to the addition of benzenesulfonyl hydrazide (0.21 g, 1.2 mmol). After the addition of hydrazide, the mixture was stirred for 3 hours at 25° C. Then the reaction was diluted with ethyl acetate (100 mL), washed with saturated sodium bicarbonate solution as well as brine, and concentrated in vacuum. The crude material was chromatographed on silica gel eluting with hexanes/ethyl acetate=2:1 to give the desired product (65% yield). MS: 322.0 (M+1 for $C_{13}H_{11}N_3O_5S_1$); mp 193–195° C.; TLC (SiO$_2$) R$_f$=0.74 (8% MeOH/CH$_2$Cl$_2$). HPLC (C18 column, 1:1 CH$_3$CN/H$_2$O+0.1 %TFA) 94.95%, RT=5.045 min. HRMS (calc for M+1) 321.0419 (found) 321.0421. IR (KBr, cm$^{-1}$): 3287, 3067, 2822, 1673, 1520, 1340, 1160, 978. $^1$H NMR (DMSO-d$_6$)δ 7.48–7.52 (m, 2H), 7.58–7.62 (m, 1H), 7.80–7.87 (m, 4H), 8.23–8.26(m,2H), 10.18(s, 1H), 11.01 (s, 1H).

EXAMPLE 2

Benzoic acid, 4-amino-2-(phenylsulfonyl)hydrazide

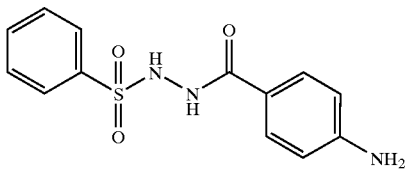

Synthesis of Example 2: Benzoic acid, 4-nitro-2-(phenylsulfonyl)hydrazide (0.82 g, Example 1) was dissolved in 50 mL of THF/EtOH (1:1), treated with wet Raney Nickel (0.6 g) and hydrogenated at 50 psi for 15 hours. The reaction was filtered, concentrated in vacuum, and chromatographed on silica gel eluting with 6% MeOH/CH$_2$Cl$_2$ to give 61 mg (84%) of the desired product. MS: 291.9 (M+1 for $C_{13}H_{13}N_3O_3S_1$); mp 171–173° C.; TLC (SiO$_2$) R$_f$=0.45 (8% MeOH/CH$_2$Cl$_2$); HPLC (C18 column, 1:1 CH$_3$CN/H$_2$O+0.01%TFA) 99.14%, RT=2.575 min. HRMS (calc for M+1) 292.0756 (found) 292.0753. IR (KBr, cm$^{-1}$): 3471, 3367, 3151, 2925, 1661,1 318, 1162. $^1$H NMR (DMSO-d$_6$) δ 5.69 (s, 2H), 6.44 (d, 2H, J=8.5 Hz), 7.32–7.58 (m, 5H), 7.75–7.80 (m, 2H), 9.68 (br, 1H), 10.12 (br, 1H).

EXAMPLE 3

Benzoic acid, 4-[[(2,4,6trichlorophenyl)sulfonyl]amino]-, 2-(phenylsulfonyl)hydrazide

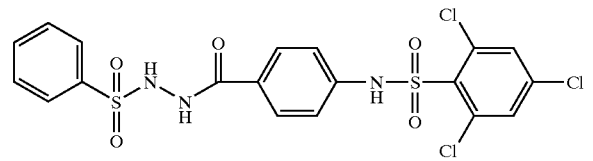

Benzoic acid, 4-amino-2-(phenylsulfonyl)hydrazide (0.15 g, 0.52 mmol, Example 2) was dissolved in 7 mL of dry pyridine, then 2,4,6-(trichlorophenyl)sulfonyl chloride (0.15 mL, 0.52 mmol) was added, and the reaction was stirred at 25° C. for overnight. The solvent was removed, and the product was recrystalized from ethyl acetate and hexane to give 0.26 g (96%) of the product as a white solid. MS: 536.0 (M+1 for $C_{19}H_{14}Cl_3N_3O_5S_2$); mp 195.7–196.2° C.; HPLC (C18 column, 1:1 MeCN/H$_2$O+0.1% TFA) 96.3%, RT=8.0 min. $^1$H NMR (DMSO-D$_6$) δ 7.10 (d, 1H, J=6.8 Hz), 7.40–7.60 (m, 7H), 7.75 (d, 1H, J=7.5 Hz), 7.79 (S, 1H), 8.63 (S, 1H), 9.92 (S, 1H), 10.49 (S, 1H), 11.35 (S, 1H).

EXAMPLE 4

Benzoic acid, 4-[[[4-(trifluoromethyl)phenyl]sulfonyl]amino]-, 2-(phenylsulfonyl)hydrazide

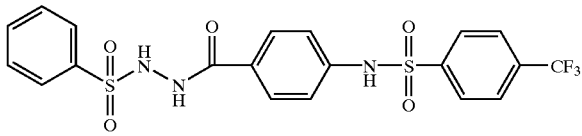

Example 4 was synthesized in accordance with the methods of Example 3 except that 4-[(trifluoromethyl)phenyl]sulfonyl chloride was used instead of 2,4,6-(trichlorophenyl)sulfonyl chloride (yield 92%). MS: 500.0 (M+1 for $C_{20}H_{16}F_3N_3O_5S_2$): mp 98.5–99.4° C.; HPLC (C18 column, 1:1 MeCN/H$_2$O+0.1% TFA) 96.8%, RT=6.1 min. $^1$H NMR (DMSO-D$_6$) δ 7.10 (d, 1H, J=8.6 Hz), 7.40–7.60 (m, 5H), 7.76 (d, 1H, J=7.5 Hz), 7.86–8.06 (m, 5H), 8.63 (d, 1H, b J=4 Hz), 9.94 (S, 1H), 10.52 (S, 1H), 10.95 (S, 1H).

EXAMPLE 5

Benzoic acid, 4-[[(3,4-dimethoxyphenyl)sulfonyl]amino]-, 2-(phenylsulfonyl)hydrazide

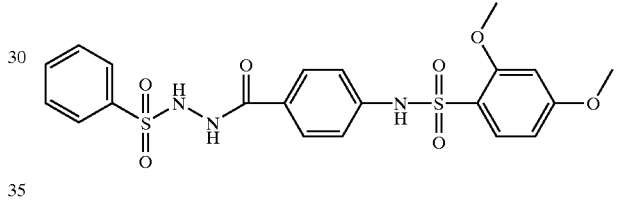

Example 5 was synthesized in accordance with the methods of Example 3 except that (3,4-dimethoxypheny)sulfonyl chloride was used instead of 2,4,6-(trichlorophenyl)sulfonyl chloride (yield 92%). MS: 492.0 (M+1 for $C_{21}H_{21}N_3O_7S_2$); mp 221.9–222.6° C.; HPLC (C18 column, 1:1 MeCN/H$_2$O+ 0.1 % TFA) 92.02%, RT=3.5 min. $^1$H NMR (DMSO-D$_6$) δ 3.72 (S, 3H), 3.75 (S, 3H), 7.01 (d, 1H, J=8.6 Hz), 7.08 (d, 2H, J=8.5 Hz), 7.25 (S, 1H), 7.32 (d, 1H, J=6.9 Hz), 7.40–7.60 (m, 5H), 7.75 (d, 2H, J=7.6 Hz), 9.91 (S, 1H), 10.48 (S, 1H), 10.52 (S, 1H).

EXAMPLE 6

Benzoic acid, 4-[[[(4-phenoxy)benzene]sulfonyl]amino]-, 2-(phenylsulfonyl)hydrazide

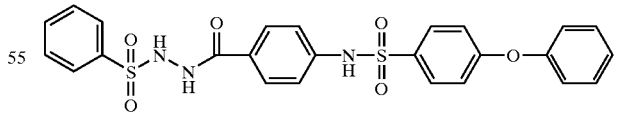

Example 6 was synthesized in accordance with the methods of Example 3 except that [(4-phenoxy)benzene]sulfonyl chloride was used instead of 2,4,6-(trichlorophenyl)sulfonyl chloride (yield 96%). MS: 524.1 (M+1 for $C_{25}H_{21}N_3O_6S_2$); mp 94.1–94.9° C; HPLC (C18 column 1:1 MeCN/H$_2$O+ 0.1% TFA, 85.08%, RT=8.7 min. $^1$H NMR (DMSO-D$_6$) δ 7.01 (d, 2H, J=4.8 Hz), 7.09 (m, 2H), 7.40–7.60 (m, 10H), 7.78 (m, 4H), 9.93 (S, 1H), 10.51 (S, 1H), 10.68 (S, 1H).

EXAMPLE 7

Benzoic acid, 4-[[(2-chloro-6-methylphenyl)sulfonyl]amino]-, 2-(phenylsulfonyl)hydrazide

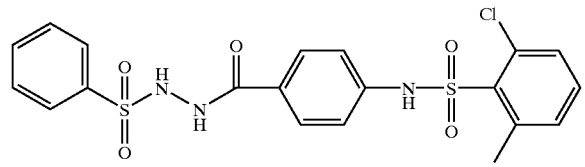

Example 7 was synthesized in accordance with the methods of Example 3 except that (2-chloro-6-methylphenyl) sulfonyl chloride was used instead of 2,4,6-(trichlorophenyl) sulfonyl chloride (yield 91%). MS: 480.1 (M+1 for $C_{20}H_{18}ClN_3O_5S_2$); mp 214.4–215.6° C.; HPLC (C18 column, 1:1 MeCN/H$_2$O+0.1%TFA) 92.5%, RT=6.3 min. CHN (calc) C, 50.05; H, 3.78; N, 8.7. (found) C, 50.18; H, 3.83; N, 8.59). $^1$H NMR (DMSO-d$_6$) δ 2.65 (S, 3H), 7.02 (d, 2H, J=8.8 Hz), 7.34 (t, 1H, J=4.9 Hz), 7.40–7.60 (m, 7H), 7.75 (d, 2H, J=7.3 Hz), 9.89 (S, 1H, 10.44 (S, 1H, 10.93 (S, 1H).

EXAMPLE 8

Benzoic acid, 4-[(methylsulfonyl)amino]-, 2-(phenylsulfonyl)hydrazide

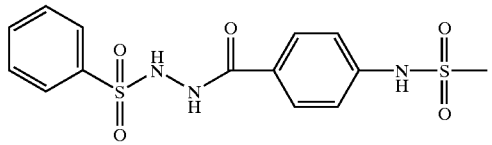

Example 8 was synthesized in accordance with the methods of Example 3 except that methylsulfonyl chloride was used instead of 2,4,6-(trichlorophenyl)-sulfonyl chloride (yield 94%). MS: 370.0 (M+1 for $C_{14}H_{15}ClN_3O_5S_2$); mp 185.6–186.5° C.; HPLC (C18 column, 1:1 MeCN/H$_2$O+0.1% TFA) 89.4%, RT=2.8 min. $^1$H NMR (DMSO-d$_6$) δ 2.91 (S, 3H), 7.18 (d, 2H, J=7.1 Hz), 7.40 (t, 2H, J=6.8 Hz), 7.50–7.60 (m, 1H, 7.63 (d, 2H, J=7.9 Hz), 7.85 (d, 2H, J=8.1 Hz), 8.88 (S, 1H), 9.89 (S, 1H), 10.63 (S, 1H).

EXAMPLE 9

Benzoic acid, 4-[[(4-methylphenyl)sulfonyl]amino]-, 2-(phenylsulfonyl)hydrazide

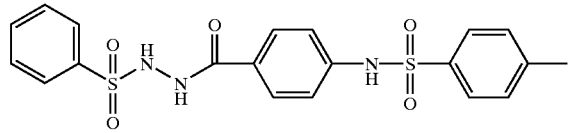

Example 9 was synthesized in accordance with the methods of Example 3 except that (4-methylphenyl)sulfonyl chloride was used instead of 2,4,6-(trichlorophenyl)sulfonyl chloride (yield 96%). MS: 446.1 (M+1 for $C_{20}H_{19}N_3O_5S_2$); mp 191.6–192.4° C.; HPLC (C18 column, 1:1 MeCN/H$_2$O+ 0.1% TFA) 95.2%, RT=4.7 min. $^1$H NMR (DMSO-d$_6$) δ 2.91 (S, 3H), 7.10 (d, 2H, J=6.8 Hz), 7.32 (d, 2H, J=5.8 Hz), 7.40–7.60 (m, 5H), 7.66 (d, 2H, J=6.1 Hz), 7.75 (d, 2H, J=8.1 Hz), 9.91 (S, 1H, 10.48 (S, 1H), 10.64 (S, 1H).

EXAMPLE 10

Benzoic acid, 4-[[(4-ethylphenyl)sulfonyl]amino]-, 2-(phenylsulfonyl)hydrazide

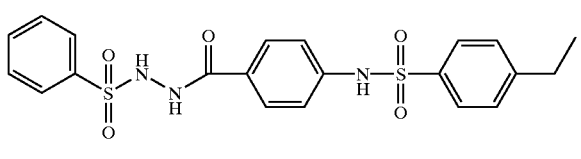

Example 10 was synthesized in accordance with the methods of Example 3 except that (4-ethylbenzene)sulfonyl chloride was used instead of 2,4,6-(trichlorophenyl)sulfonyl chloride (yield 92%). MS: 460.1 (M+1 for $C_{21}H_2N_{13}O_5S_2$); mp 142.3–142.9° C.; HPLC (C18 column, 1:1 MeCN/H$_2$O+ 0.1% TFA) 93.5%, RT=5.9 min. $^1$H NMR (DMSO-d$_6$) δ 1.11 (t, 3H, J=7.6 Hz), 2.59 (q, 2H, J=7.5 Hz), 7.10 (d, 2H, J=8.6 Hz), 7.35 (d, 2H, J=8.0Hz), 7.40–7.60 (m, 5H), 7.68 (d, 2H, J=8.1 Hz), 7.75 (d, 2H, J=7.5 Hz), 9.91 (S, 1H, 10.48 (S, 1H), 10.68 (S, 1H).

EXAMPLE 11

Benzoic acid, 4-[[(4-n-propylphenyl)sulfonyl]amino]-, 2-(phenylsulfonyl)hydrazide

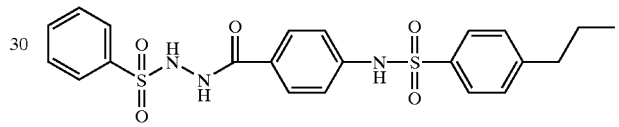

Example 11 was synthesized in accordance with the methods of Example 3 except that (4-n-propylbenzene)sulfonyl chloride was used instead of 2,4,6-(trichlorophenyl)sulfonyl chloride (yield 90%). MS: 474.1 (M+1 for $C_{22}H_{23}N_3O_5S_2$); HPLC (C18 column, 1:1 MeCN/H$_2$O+ 0.1% TFA) 95.3%, RT=7.4 min. $^1$H NMR (DMSO-d$_6$) δ 0.79 (t, 3H, J=7.5 Hz), 1.25 (M, 2H), 2.59 (q, 2H, J=7.5 Hz), 7.10 (d, 2H, J=8.6 Hz), 7.35 (d, 2H, J=8.0 Hz), 7.40–7.60 (m, 5H), 7.68 (d, 2H, J=8.1 Hz), 7.75 (d, 2H, J=7.5 Hz), 9.91 (S, 1H, 10.46 (S, 1H), 10.68 (S, 1H).

EXAMPLE 12

Benzoic acid, 4-[[(4-n-butylphenyl)sulfonyl]amino]-, 2-(phenylsulfonyl)hydrazide

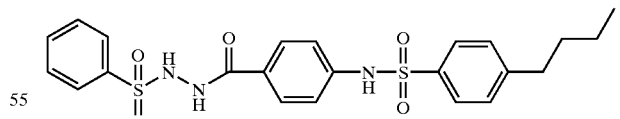

Example 12 was synthesized in accordance with the methods of Example 3 except that (4-n-butylbenzene) sulfonyl chloride was used instead of 2,4,-(trichlorophenyl)-sulfonyl chloride (yield 92%). MS: 488.1 (M+1 for $C_{23}H_{25}N_3O_5S_2$); mp 76.0–77.1° C.; HPLC (C18 column, 1:1 MeCN/H$_2$O+0.1% TFA) 94.0%, RT=9.9 min. $^1$H NMR (DMSO-d$_6$) δ 0.82 (t, 3H, J=7.4 Hz), 1.22 (m, 2H, J=7.6 Hz), 1.48 (m, 2H, J=7.8 Hz), 2.56 (t, 2H, J=7.6 Hz), 7.10 (d, 2H, J=8.8 Hz), 7.35 (d, 2H, J=8.1 Hz), 7.40–7.60 (m, 5H), Benzoic acid, 4-[[(4-n-pentylphenyl)sulfonyl]amino]-, 2-(phenylsulfonyl)hydrazide

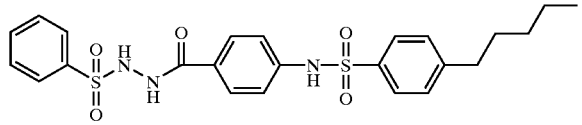

Example 13 was synthesized in accordance with the methods of Example 3 except that (4-n-pentylbenzene) sulfonyl chloride was used instead of 2,4,6-(trichlorophenyl)-sulfonyl chloride (yield 90%). MS: 502.1 (M+1 for $C_{24}H_{27}N_3O_5S_2$); mp 97.1–97.9° C.; HPLC (C18 column, 1:1 MeCN/H$_2$O+0.1% TFA) 95.0%, RT=1.5 min. $^1$H NMR (DMSO-D$_6$) δ 0.85 (t, 3H, J=6.6 Hz), 1.28 (m, 4H, J=6.6 Hz), 1.56 (m, 2H, J=7.1 Hz), 2.59 (t, 2H, J=7.6 Hz), 7.07 (d, 2H, J=8.6 Hz), 7.24 (d, 2H, J=9.5 Hz), 7.41 (t, 2H, J=7.8 Hz), 7.50–7.70 (m, 3H), 7.71 (d, 2H, J=8.3 Hz), 7.92 (d, 2H, J=8.3 Hz), 9.90 (S, 1H, 10.46 (S, 1H), 10.64 (S, 1H).

EXAMPLE 14
Benzoic acid, 4-[[(4-fluorophenyl)sulfonyl]amino]-, 2-(phenylsulfonyl)hydrazide

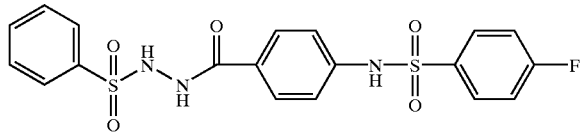

Example 14 was synthesized in accordance with the methods of Example 3 except that (4-fluorobenzene) sulfonyl chloride was used instead of 2,4,6-(trichlorophenyl)-sulfonyl chloride. MS: 450.1 (M+1 for $C_{19}H_{16}FN_3O_5S_2$); mp 183.5–185.0° C.; HPLC (C18 column, 1:1 MeCN/H$_2$O+0.1% TFA) 97.9%, RT=4.4 min. CHN (calc) C, 50.77; H, 3.59; N, 9.35. (found) C, 50.58; H, 3.65; N, 9.05. $^1$H NMR (DMSO-d$_6$) δ 7.09 (d, 2H, J=8.6 Hz), 7.37 (t, 2H, J=6.6 Hz), 7.46 (t, 2H, J=7.9 Hz), 7.58 J=4.1 Hz), 7.76 (d, 2H, J=3.1 Hz), 7.80–7.90 (m, 3H), 9.92 (S, 1H, 10.49 (S, 1H), 10.72 (S, 1H).

EXAMPLE 15
Benzoic acid, 4-[(phenylsulfonyl)]amino]-, 2-(phenylsulfonyl)hydrazide

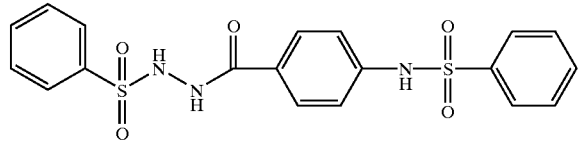

Example 15 was synthesized in accordance with the methods of Example 3 except that benzenesulfonyl chloride was used instead of 2,4,-(trichlorophenyl)sulfonyl chloride. MS: 432.0 (M+1 for $C_{19}H_{17}N_3O_5S_2$); mp 140.8–144.5° C.; HPLC (C18 column, 1:1 MeCN/H$_2$O+0.1% TFA) 97.9%, RT=4.2 min. CHN (calc) C, 52.89; H, 3.97; N, 9.74. (found) C, 53.41; H, 3.95; N, 9.77. $^1$H NMR (DMSO-d$_6$) δ 7.20 (d, 2H, J=8.8 Hz), 7.50–7.70 (m, 8H), 7.80–7.95 (m, 4H), 10.01 (S, 1H, 10.58 (S, 1H, 10.82 (S, 1H).

EXAMPLE 16
4-Benzylamino-benzoic acid 2-(phenylsulfonyl)hydrazide

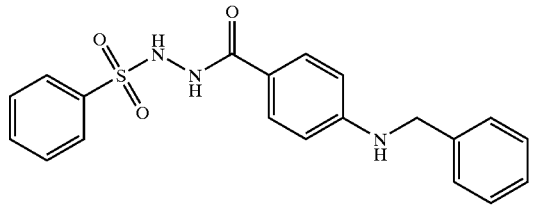

4Aminobenzoic acid 2-(phenylsulfonyl)hydrazide (100 mg, 0.34 mmol) was dissolved in THF (3.4 mL), treated with acetic acid (20 μL, 0.34 mmol) and benzaldehyde (23 μL, 0.34 mmol), and stirred for 5 minutes. Sodium triacetoxyborohydride (87 mg, 0.41 mmol) was added, and the reaction was stirred overnight. The reaction was diluted with EtOAc (100 mL), washed with saturated sodium bicarbonate solution and brine, dried over Na$_2$SO$_4$, and concentrated in vacuo. The residue was chromatographed on silica gel eluting with 3:2 hexanes/EtOAc to give 23 mg (18%) of the desired product. MS: 382.0 (M+1 for $C_{20}H_{19}N_3O_3S_1$); mp 214–215° C.; TLC (SiO$_2$) R$_f$=0.43 (1:1 hexane/EtOAc); HPLC (C18 column, 1:1 CH$_3$CN/H$_2$O+0.1% TFA) 99.04%, RT=8.309 min. HRMS (calc) 382.1225 (found) 382.1222; IR (KBr, cm$^{-1}$): 3404, 3355, 3107, 1657, 1607, 1159. $^1$H NMR (DMSO-d$_6$) δ 4.25 (d, 2H, J=5.6 Hz), 6.47 (d, 2H, J=8.3 Hz), 6.86–6.88 (m, 1H), 7.26–7.28 (m, 4H), 7.37–7.40 (m, 2H), 7.42–7.45 (m, 2H), 7.52–7.56 (m, 1H), 7.74 (d, 2H, J=7.8 Hz), 9.58 (s, 1H) 9.68 (s, 1H, 10.13 (s, 1H).

EXAMPLE 17
Benzoic acid, 4-[[(3-methylphenyl)sulfonyl]amino]-, 2-(phenylsulfonyl)hydrazide

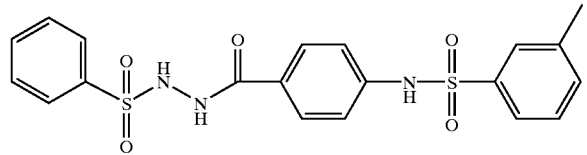

Example 17 was synthesized in accordance with the methods of Example 3 except that (3-methylphenyl)sulfonyl chloride was used instead of 2,4,6-(trichlorophenyl)sulfonyl chloride (yield 96%). MS: 446.1 (M+1 for $C_{20}H_{19}N_3O_5S_2$); mp 219.0–219.7° C. HPLC (C18 column, 1:1 MeCN/H$_2$O+ 0.1% TFA) 98.8%, RT=5.2 min. $^1$H NMR (DMSO-d$_6$) δ 2.31 (S, 3H), 7.09 (d, 2H, J=8.6 Hz), 7.40–7.60 (m, 9H), 7.75 (d, 2H, J=7.3 Hz), 9.91 (S, 1H, 10.48 (S, 1H), 10.68 (S, 1H).

EXAMPLE 18
4-Phenoxybenzoic acid, 2-[(3-methyl)phenylsulfonyl]hydrazide

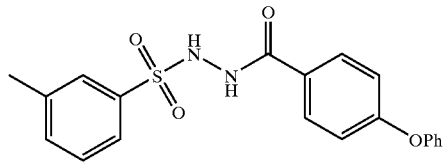

A solution of 2-phenoxybenzoic acid hydrazide (0.3 M) in pyridine (0.513 mL) was treated with a solution of the 3-(methylphenyl)sulfonyl chloride (1.0 M) in CH$_2$Cl$_2$ (0.225 mL). The reaction was placed in a Bohdan Miniblock apparatus and shaken at 45° C. for 16 hours. The reaction was cooled to room temperature, treated with polymer-supported polyamine quench resin (Aldrich, 100 mg), and shaken for 16 hours. The solution was filtered and concentrated. The residue was purified by preparative HPLC on a Phenomenex Develofil 28×100 mm C-18 column eluting with a gradient of 10% to 100% CH$_3$CN/H$_2$O+3% n-propanol. MS: 384 (M+1 for C$_{20}$H$_{18}$N$_2$O$_4$S); HPLC (Waters Alliance 2790 column, solvent gradient of 60% to 100% CH$_3$CN/H$_2$O+0.1% formic acid. Purity: 100%.

EXAMPLE 19
4-Phenoxybenzoic acid, 2-[3-bromophenylsulfonyl]hydrazide

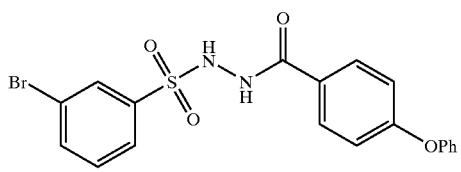

A solution of 2-phenoxybenzoic acid hydrazide (0.3 M) in pyridine (0.513 mL) was treated with a solution of the 3-(bromophenyl)sulfonyl chloride (1.0 M) in CH$_2$Cl$_2$ (0.225 mL). The reaction was placed in a Bohdan Miniblock apparatus and shaken at 45° C. for 16 hours. The reaction was cooled to room temperature, treated with polymer-supported polyamine quench resin (Aldrich, 100 mg), and shaken for 16 hours. The solution was filtered and concentrated. The residue was purified by preparative HPLC on a Phenomenex Develofil 28×100 mm C-18 column eluting with a gradient of 10% to 100% CH$_3$CN/H$_2$O+3% n-propanol. MS: 448 (M+1 for C$_{19}$H$_{15}$BrN$_2$O$_4$S); HPLC (Waters Alliance 2790 column, solvent gradient of 60% to 100% CH$_3$CN/H$_2$O+0.1% formic acid. Purity: 96%.

EXAMPLE 20
4-Phenoxybenzoic acid, 2-[2-chlorophenylsulfonyl]hydrazide

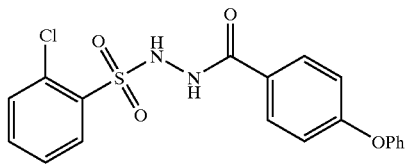

A solution of 2-phenoxybenzoic acid hydrazide (0.3 M) in pyridine (0.513 mL) was treated with a solution of the 2-(chlorophenyl)sulfonyl chloride (1.0 M) in CH$_2$Cl$_2$ (0.225 mL). The reaction was placed in a Bohdan Miniblock apparatus and shaken at 45° C. for 16 hours. The reaction was cooled to room temperature, treated with polymer-supported polyamine quench resin (Aldrich, 100 mg), and shaken for 16 hours. The solution was filtered and concentrated. The residue was purified by preparative HPLC on a Phenomenex Develofil 28×100 mm C-18 column eluting with a gradient of 10% to 100% CH$_3$CN/H$_2$O+3% n-propanol. MS: 403 (M+1 for C$_{19}$H$_{15}$ClN$_2$O$_4$S); HPLC (Waters Alliance 2790 column, solvent gradient of 60% to 100% CH$_3$CN/H$_2$O+0.1% formic acid. Purity: 98%.

EXAMPLE 21
4-Phenoxybenzoic acid, 2-[2-(trifluoromethoxy)phenylsulfonyl]hydrazide

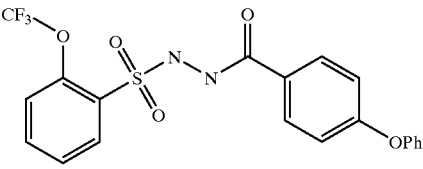

A solution of 2-phenoxybenzoic acid hydrazide (0.3 M) in pyridine (0.513 mL) was treated with a solution of the 2-(trifluoromethoxy)phenylsulfonyl chloride (1.0M) in CH$_2$Cl$_2$ (0.225 mL). The reaction was placed in a Bohdan Miniblock apparatus and shaken at 45° C. for 16 hours. The reaction was cooled to room temperature, treated with polymer-supported polyamine quench resin (Aldrich, 100 mg), and shaken for 16 hours. The solution was filtered and concentrated. The residue was purified by preparative HPLC on a Phenomenex Develofil 28×100 mm C-18 column eluting with a gradient of 10%/ to 100% CH$_3$CN/H$_2$O+3% n-propanol. MS: 453 (M+1 for C$_{20}$H$_{15}$F$_3$N$_2$O$_5$S); HPLC (Waters Alliance 2790 column, solvent gradient of 60% to 100% CH$_3$CN/H$_2$O+0.1% formic acid. Purity: 95%.

EXAMPLE 22
4-Phenoxybenzoic acid, 2-[(4-methyl-3-nitro)phenylsulfonyl]hydrazide

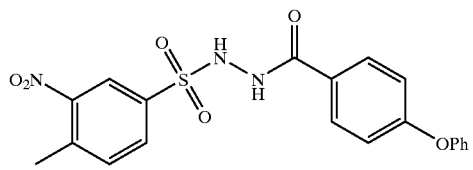

A solution of 2-phenoxybenzoic acid hydrazide (0.3 M) in pyridine (0.513 mL) was treated with a solution of the (4-methyl-3-nitro)phenylsulfonyl chloride (1.0 M) in CH$_2$Cl$_2$ (0.225 mL). The reaction was placed in a Bohdan Miniblock apparatus and shaken at 45° C. for 16 hours. The reaction was cooled to room temperature, treated with polymer-supported polyamine quench resin (Aldrich, 100 mg), and shaken for 16 hours. The solution was filtered and concentrated. The residue was purified by preparative HPLC on a Phenomenex Develofil 28×100 mm C-18 column eluting with a gradient of 10% to 100% CH$_3$CN/H$_2$O+3% n-propanol. MS: 428 (M+1 for C$_{10}$H$_{17}$N$_3$O$_6$S); HPLC (Waters Alliance 2790 column, solvent gradient of 60% to 100% CH$_3$CN/H$_2$O+0.1% formic acid. Purity: 94%.

EXAMPLE 23
4-Phenoxybenzoic acid, 2-[2-trifluorophenylsulfonyl]hydrazide

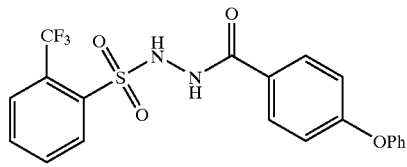

A solution of 2-phenoxybenzoic acid hydrazide (0.3 M) in pyridine (0.513 mL) was treated with a solution of the 2-trifluorophenylsulfonyl chloride (1.0 M) in CH$_2$Cl$_2$ (0.225 mL). The reaction was placed in a Bohdan Miniblock apparatus and shaken at 45° C. for 16 hours. The reaction was cooled to room temperature, treated with polymer-supported polyamine quench resin (Aldrich, 100 mg), and shaken for 16 hours. The solution was filtered and concentrated. The residue was purified by preparative HPLC on a Phenomenex Develofil 28×100 mm C-18 column eluting with a gradient of 10% to 100% CH$_3$CN/H$_2$O+3% n-propanol. MS: 437 (M+1 for C$_{20}$H$_{15}$F$_3$N$_2$O$_4$S$_1$); HPLC (Waters Alliance 2790 column, solvent gradient of 60% to 100% CH$_3$CN/H$_2$O+0.1% formic acid. Purity: 97%.

EXAMPLE 24

4-(1,1-Dimethylethyl)-benzoic acid, 2-(phenylsulfonyl) hydrazide

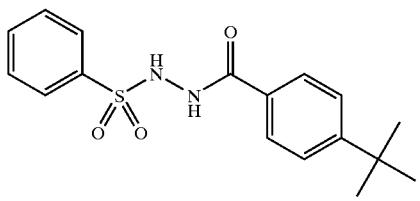

Step 1: The Preparation of 4-tert-butyl-benzoic acid hydrazide

A solution of 4-tert-butyl benzoic acid (0.2 g, 1.2 mmol in 10 mL of dry THF) cooled to 0° C. and treated with N-methyl-morpholine (1.6 mL, 14.6 mmol) as well as isobutyl chloroformate (1.7 mL, 1.3 mmol). Then the mixture was stirred for 10 minutes at 0° C. After hydrazine (0.6 g, 3.6 mmol) was added to the reaction mixture, it was stirred 3 hours at 25° C. The reaction was then diluted with ethyl acetate (100 mL), washed with saturated sodium bicarbonate solution as well as brine, and concentrated in vacuum. The crude material was chromatographed on silica gel eluting with hexanes/ethyl acetate=2:1 to give 4-tert-butyl-benzoic acid hydrazide.

Step 2: The Preparation of 4-(1,1-dimethylethyl)-benzoic acid, 2-(phenylsulfonyl)hydrazide (Example 24)

4-tert-Butyl-benzoic acid hydrazide (0.5 g, 2.60 mmol) was dissolved in THF (29 mL). N,N-diisopropylethylamine (1.81 mL, 10.4 mmol) was added, and the reaction was cooled to 0° C. Phenylsulfonyl chloride (0.36 mL, 2.86 mmol) was added followed by DMAP (5 mg, 0.04 mmol). The reaction was allowed to warm to room temperature, and the reactants all dissolved. The solution went from a yellow color to a deep red over the course of 4 hours. The reaction was then concentrated down and purified by flash chromatography eluting with 3:1 hexanes/EtOAc. The desired product was isolated (0.32 g, 37.1%). MS: 333.1 (M+1 for C$_{17}$H$_{20}$N$_2$O$_3$S); mp 197–199° C.; TLC: SiO$_2$ R$_f$=0.56 (1:1 hexane/EtOAc). Analysis C$_{17}$H$_{20}$N$_2$O$_3$S: (calc) C, 61.42; H, 6.06; N, 8.43. (found) C, 61.38; H, 6.09; N, 8.27. IR (KBr, cm$^{-1}$) 3213, 2965, 1648, 1403, 1349, 1179. $^1$H NMR (400 MHz, CDCl$_3$) δ 1.29 (s, 9H), 7.39–7.55 (m, 8H), 7.92–7.93 (m, 2H), 8.06 (s, 1H).

EXAMPLE 25

[1,1'-Biphenyl]-4-carboxylic acid, 2-(phenylsulfonyl) hydrazide

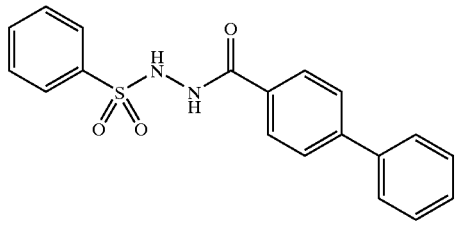

Biphenyl-4-carboxylic acid hydrazide (0.5 g, 2.36 mmol) was suspended in THF (26 mL). N,N-diisopropylethylamine (1.64 mL, 9.44 mmol) was added, and the reaction was cooled to 0° C. Phenylsulfonyl chloride (0.33 mL, 2.59 mmol) was added followed by DMAP (5 mg, 0.04 mmol). The reaction was allowed to warm to room temperature. The solution was orange after it stirred for 1 hour; DMF (5 mL) was added, and the solution became clear. After 3 hours of stirring, the solution was diluted with EtOAc (150 mL). It was then washed with saturated sodium bicarbonate and brine and dried over Na$_2$SO$_4$. The reaction was then concentrated down and triturated with CH$_2$Cl$_2$. The desired product was isolated (0.19 g, 22.7%). MS: 351.1 (M−1 for C$_{19}$H$_{16}$N$_2$O$_3$S); mp 216–219° C. TLC: SiO$_2$, R$_f$=0.55 (1:1 hexane/EtOAc). Analysis C$_{19}$H$_{16}$N$_2$O$_3$S.0.25 H$_2$O: (calc) C, 63.94; H, 4.66; N, 7.85. (found) C, 63.76; H, 4.64; N, 7.76. HPLC: (30% H$_2$O/70% CH$_3$CN/0.1% TFA), RT=3.731 min. Purity: 94.16%. IR (KBr, cm$^{-1}$) 3337, 3035, 2811, 1655, 1340, 1156. $^1$H NMR (400 MHz, DMSO) δ 7.26–8.00 (m, 14H), 10.01 (s, 1H, 10.71 (s, 1H).

EXAMPLE 26

3-Phenoxybenzoic acid, 2-(phenylsulfonyl)hydrazide

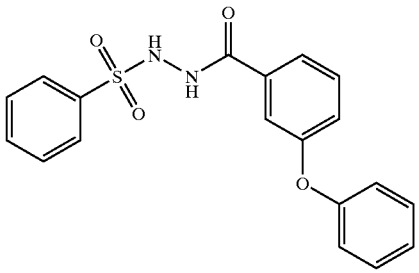

Example 26 was synthesized in accordance with the methods of Example 24 except that 3-phenoxybenzoic acid was used instead of 4-tert-butyl-benzoic acid. MS: 369.0 (M+1 for C$_{19}$H$_{16}$N$_2$O$_4$S$_1$); amorphous solid; TLC (SiO$_2$) R$_f$=0.35 (5% MeOH/CH$_2$Cl$_2$); HPLC (C18 column, 1:1 CH$_3$CN/H$_2$O+0.1% TFA) 98.31%, RT=8.863 min. HRMS (calc) 369.0907 (found) 369.0913. IR (KBr, cm$^{-1}$): 3309, 3147, 1673, 1165. $^1$H NMR (DMSO-d$_6$) δ 7.00 (d, 2H, J=8.3 Hz), 7.13–7.19 (m, 3H), 7.38–7.41 (m, 4H), 7.43–7.50 (m, 2H), 7.56–7.59 (m, 1H, 7.76 (d, 2H, J=8.1 Hz), 9.99 (s, 1H), 10.09 (s, 1H).

EXAMPLE 27
2-Phenoxybenzoic acid, 2-(phenylsulfonyl)hydrazide

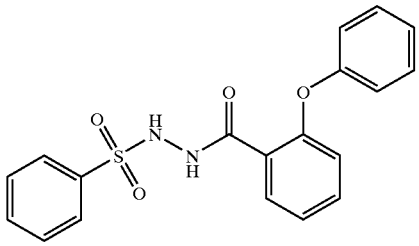

Example 27 was synthesized in accordance with the methods of Example 24 except that 2-phenoxybenzoic acid was used instead of 4-tert-butyl-benzoic acid. MS: 369.0 (M+1 for $C_{19}H_{16}N_2O_4S_1$); mp 149–150° C.; TLC (SiO$_2$) $R_f$=0.67 (2:1 hexane/EtOAc); HPLC (C18 column, 1:1 CH$_3$CN/H$_2$O+0.1% TFA) 99.02%, RT=19.912 min. Analysis $C_{19}H_{16}N_2O_4S_1$: (calc) C, 61.94; H, 4.38; N, 7.60. (found) C, 61.77; H, 4.33; N, 7.57. IR (KBr, cm$^{-1}$): 3368, 3166, 1667, 1479, 1160. $^1$H NMR (CDCl$_3$) δ 6.80 (d, 1H, J=8.3 Hz), 7.03–7.12 (m, 3H), 7.25–7.27 (m, 1H, 7.36–7.46 (m, 5H), 7.51–7.59 (m, 2H), 7.76–7.83 (m, 3H), 9.39 (d, 1H, J=6.6 Hz).

EXAMPLE 28
4-Phenoxybenzoic acid, 2-(phenylsulfonyl)hydrazide

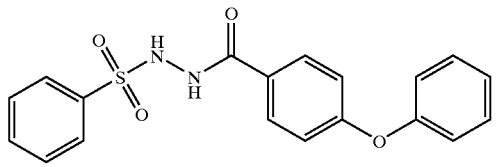

Example 28 was synthesized in accordance with the methods of Example 24 except that 4-phenoxybenzoic acid was used instead of 4-tert-butyl-benzoic acid. MS: 369.0 (M+1 for $C_{19}H_{16}N_2O_4S_1$); mp glassy solid; TLC (SiO$_2$) $R_f$=0.70 (1:1 hexane/EtOAc); HPLC (C18 column, 70:30 CH$_3$CN/H$_2$O+0.1% TFA) 94.87%, RT=3.752 min. HRMS (calc for M+1) 367.0753 (found) 367.0743. IR (KBr, cm$^{-1}$): 3324, 2964, 1723, 1164. $^1$H NMR (DMSO-d$_6$) δ 6.92–6.95 (m, 2H), 7.03–7.06 (m, 2H), 7.16–7.20 (m, 1H), 7.38–7.79 (m, 9H), 9.96 (s, 1H), 10.59 (s, 1H).

EXAMPLE 29
4-Benzyloxybenzoic acid, 2-phenylsulfonyl)hydrazide

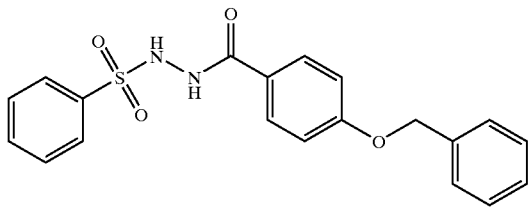

Example 29 was synthesized in accordance with the methods of Example 24 except that 4-benzyloxybenzoic acid was used instead of 4-tert-butyl-benzoic acid. MS: 383.0 (M+1 for $C_{20}H_{18}N_2O_4S_1$); mp 159–160° C.; TLC (SiO$_2$) $R_f$=0.48 (1:1 hexane/EtOAc); HPLC (C18 column, 1:1 CH$_3$CN/H$_2$O+0.1% TFA) 99.85%, RT=11.663 min. IR (KBr, cm$^{-1}$): 3403, 3340, 3124, 2941, 1657, 1422, 1165. Analysis $C_{19}H_{19}N_3O_3S_1$: (calc) C, 62.81; H, 4.74; N, 7.32. (found) C, 62.76; H, 4.78; N, 7.31. $^1$H NMR (DMSO-d$_6$) δ 5.11 (s, 2H), 7.00 (d, 2H, J=8.8 Hz), 7.27–7.41 (m, 5H), 7.45–7.49 (m, 2H), 7.55–7.63 (m, 3H), 7.78 (d, 2H, J=7.3 Hz), 9.88 (br, 1H), 10.49 (br, 1H).

EXAMPLE 30
Benzoic acid, 4-[[(4-methoxyphenyl)sulfonyl]amino]-, 2-(phenylsulfonyl)hydrazide

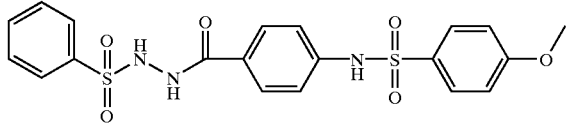

Example 30 was synthesized in accordance with the methods of Example 3 except that (4-methoxybenzene)sulfonyl chloride was used instead of 2,4,6-(trichlorophenyl)sulfonyl chloride (yield 90%). MS: 462.1 (M+1 for $C_{20}H_{19}N_3O_6S_2$); mp 164.3–164.9° C.; HPLC (C18 column, 1:1 MeCN/H$_2$O=0.1% TFA) 99.8%, RT=4.2 min. $^1$H NMR (DMSO-d$_6$) δ 3.13 (S, 3H), 7.04 (d, 4H, J=10.2 Hz), 7.40–7.60 (m, 5H), 7.75 (m, 4H), 9.91 (S, 1H), 10.48 (S, 1H, 10.57 (S, 1H).

EXAMPLE 31
4-Iodo-benzoic acid, 2-(phenylsulfonyl)hydrazide

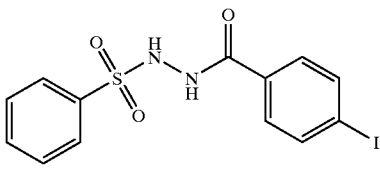

4-Iodo-benzoic acid, 2-(phenylsulfonyl)hydrazide was synthesized in accordance with the methods of Example 24, except that 4-iodo-benzoic acid was used instead of 4-nitro-benzoic acid. MS: 402.9 (M+1 for $C_{13}H_{11}N_2O_3S_1I_1$); mp: 193–195° C.; TLC (SiO$_2$) $R_f$=0.77 (8% MeOH/CH$_2$Cl$_2$); HPLC (C18 column, 1:1 CH$_3$CN/H$_2$O+0.1% TFA) 95.71%, RT=7.334 min. HRMS (calc for M+1) 402.9613 (found) 402.9625. IR (KBr, cm$^{-1}$): 3331, 3151, 1645, 1377, 1171. $^1$H NMR (DMSO-d$_6$) δ 7.39–7.41 (m, 2H), 7.46–7.52 (m, 2H), 7.54–7.60 (m, 1H, 7.74–7.80 (m, 4H), 10.02, (d, 1H, J=3.6Hz), 10.72-(d, 1H, J=3.6 Hz).

EXAMPLE 32
4-Phenacetylenyl-benzoic acid, 2-(phenylsulfonyl)hydrazide

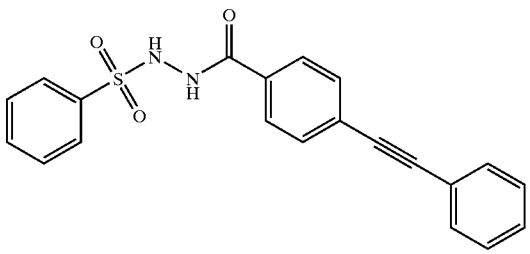

4-Iodo-benzoic acid, 2-(phenylsulfonyl)hydrazide (75 mg, 0.19 mmol, Example 31) was dissolved in THF (2.5 mL) and treated with Et$_3$N (174 µL, 1.25 mmol), phenylacetylene (41 µL, 0.37 mmol), bis-triphenylphosphine palladium (II) dichloride, and copper (I) iodide (2.4 mg, 0.013 mmol). The reaction was stirred overnight at room temperature, then diluted with EtOAc (100 mL), washed with saturated sodium bicarbonate solution and brine, dried over Na$_2$SO$_4$, and concentrated in vacuo. The residue was chromatographed on silica gel eluting with 3% MeOH/CH$_2$Cl$_2$ to give 70 mg (97%) of the desired product. MS: 377.1 (M+1 for C$_{21}$H$_{16}$N$_2$O$_3$S$_1$); mp 175° C. (dec); TLC (SiO$_2$) R$_f$=0.50 (4% MeOH/CH$_2$Cl$_2$); HPLC (C18 column, 7:3 CH$_3$CN/H$_2$O+0.1% TFA) 94.87%, RT=4.677 min. HRMS (calc for M+1) 377.0960 (found) 377.0958. IR (KBr, cm$^{-1}$): 3324, 3059, 2812, 1658, 1341, 1158. $^1$H NMR (DMSO-d$_6$) δ 7.39–7.43 (m, 3H), 7.48–7.61 (m, 7H), 7.68 (d, 2H, J=8.3 Hz), 7.79–7.81 (m, 2H), 10.45 (br, 1H), 10.75 (br, 1H).

EXAMPLE 33
Phenethyl-benzoic acid, 2-(phenylsulfonyl)hydrazide

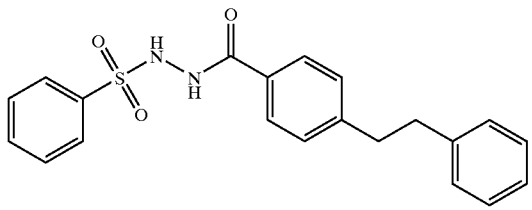

4-Phenacetylenyl-benzoic acid, 2-(phenylsulfonyl) hydrazide (128 mg, 0.34 mmol, Example 32) was dissolved in MeOH (10 mL) and THF (26 mL), treated with 20% Pd/C (30 mg), and shaken under an atmosphere of H$_2$ (50 psi) for 16 hours. The reaction was filtered and concentrated, then washed with saturated sodium bicarbonate solution and brine, dried over Na$_2$SO$_4$, and concentrated in vacuum. The residue was chromatographed on silica gel eluting with 4% MeOH/CH$_2$Cl$_2$ to give 125 mg (97%) of the desired product. MS: 381.0 (M+1 for C$_{21}$H$_{20}$N$_2$O$_3$S$_1$); mp 158–159° C.; TLC (SiO$_2$) R$_f$=0.48 (8% MeOH/CH$_2$Cl$_2$); HPLC (C18 column, 7:3 CH$_3$CN/H$_2$O+0.1% TFA) 98.40%, RT=4.544 min. HRMS (calc for M+1) 381.1273 (found) 381.1270. IR (KBr, cm$^{-1}$): 3338, 3134, 1665, 1166. $^1$H NMR (DMSO-d$_6$) δ 2.81–2.89 (m, 4H), 7.11–7.26 (m, 7H), 7.46–7.60 (m, 5H), 7.77–7.80 (m, 2H), 9.94 (br, 1H, 10.57 (br, 1H).

EXAMPLE 34
4-(3-Cyclohexyl-1-propynyl)-benzoic acid, 2-(phenylsulfonyl)hydrazide

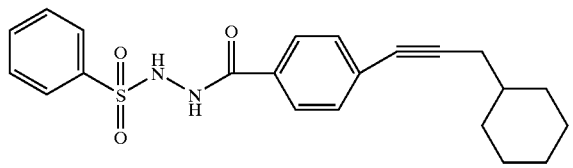

Example 34 was synthesized in accordance with the methods of Example 32, except that 3-cyclohexyl-1-propyne was used instead of phenylacetylene. MS: 397 (M+1 for C$_{22}$H$_{24}$N$_2$O$_3$S$_1$); mp 180–182° C.; TLC (SiO$_2$) R$_f$=0.4 (50% EtOAc/hexanes); HPLC (C18 column, 7:3 CH$_3$CN/H$_2$O+ 0.1% TFA) 98%, RT=9.9 min. $^1$H NMR (DMSO-d$_6$) δ 0.95–1.24 (m, 5H), 1.43–1.74 (m, 5H), 2.30 (s, 1H), 2.31 (s, 1H, 7.39 (d, 2H, J=8.6 Hz), 7.46–7.50 (m, 2H), 7.56–7.59 (m, 3H), 7.83 (d, 2H, J=7.3 Hz), 10.00 (s, 1H), 10.70 (s, 1H).

EXAMPLE 35
4-(3-Cyclohexyl-3-hydroxy-1-propynyl)-benzoic acid, 2-(phenylsulfonyl)hydrazide

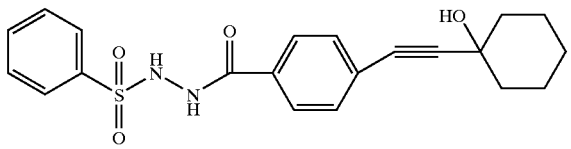

Example 35 was synthesized in accordance with the methods of Example 32, except that 3-cyclohexyl-3-hydroxy-1-propyne was used instead of phenylacetylene. MS: 399 (M+1 for C$_{21}$H$_{22}$N$_2$O$_4$S$_1$); mp 96–97° C.; TLC (SiO$_2$) R$_f$=0.3 (50% EtOAc/hexanes); HPLC (C18 column, 7:3 CH$_3$CN/H$_2$O+0.1%TFA) 99%, RT=5.0 min. $^1$H NMR (DMSO-d$_6$) δ 1.10–1.85 (m, 10H), 5.45 (s, 1H), 7.33–7.50 (m, 4H), 7.52–7.78 (m, 3H), 8.04 (d, 2H, J=7.5 Hz), 10.00 (s, 1H), 10.71 (s, 1H).

EXAMPLE 36
4-(3-Cyclohexyl-3-hydroxy-1-propyl)-benzoic acid, 2-(phenylsulfonyl)hydrazide

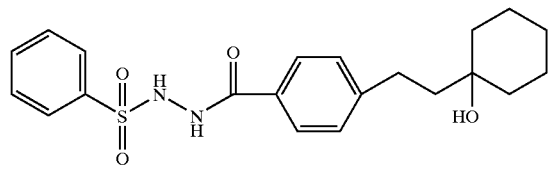

Example 36 was synthesized in accordance with the methods of Example 33, except that 4-(3-cyclohexyl-3-hydroxy-1-propynyl)-benzoic acid, 2-(phenylsulfonyl) hydrazide (Example 35) was used instead of 4phenacetylenyl-benzoic acid, 2-(phenylsulfonyl)hydrazide. MS: 403 (M+1 for C$_{21}$H$_{26}$N$_2$O$_4$S$_1$); mp 158–159° C.; TLC (SiO$_2$) R$_f$=0.3 (50% EtOAc/hexanes); HPLC (C18 column, 7:3 CH$_3$CN/H$_2$O+0.1%TFA) 95%, RT=5.0 min. $^1$H NMR (DMSO-d$_6$) δ 1.10–1.65 (m, 12H), 2.46–2.61 (m, 2H), 4.00 (s, 1H), 7.20 (d, 2 H, J=8.1 Hz), 7.46–7.57 (m, 5H), 7.78 (d, 2H, J=7.3 Hz), 9.93 (s, 1H), 10.56 (s, 1H).

EXAMPLE 37
4-(3,3-Dimethyl-1-butynyl)benzoic acid, 2-(phenylsulfonyl)hydrazide

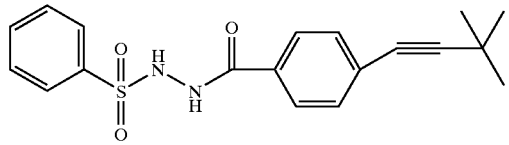

Example 37 was synthesized in accordance with the methods of Example 32, except that 3,3-dimethylbutyne was used instead of phenylacetylene. MS: 357 (M+1 for C$_{19}$H$_{20}$N$_2$O$_3$S$_1$); mp 160° C. (dec.); TLC (SiO$_2$) R$_f$=0.5 (50% EtOAc/hexanes); HPLC (C18 column, 7:3 CH$_3$CN/ H$_2$O+0.1% TFA) 96%, RT=12 min. $^1$H NMR (DMSO-d$_6$) δ 1.23 (s, 9H), 7.49 (d, 2H, J=8.15 Hz), 7.45–7.50 (m, 2H), 7.55–7.60 (m, 3H), 7.77 (d, 2H, J=7.5 Hz), 9.99 (s, 1H, 10.67 (s, 1H).

EXAMPLE 38

4-(3,3-Dimethyl-1-butyl)-benzoic acid, 2-(phenylsulfonyl)hydrazide

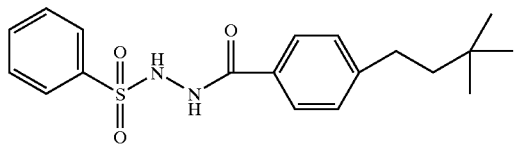

Example 38 was synthesized in accordance with the methods of Example 33, except that 4-(3,3-dimethyl-1-butynyl)benzoic acid, 2-(phenylsulfonyl)hydrazide (Example 37) was used instead of 4-phenacetylenyl-benzoic acid, 2-(phenylsulfonyl)hydrazide. MS: 361 (M+1 for $C_{19}H_{24}N_2O_3S_1$); mp 168–169° C.; TLC ($SiO_2$) $R_f$=0.7 (50% EtOAc/hexanes); HPLC (phenol hexal column, 1:1$CH_3CN$/$H_2O$+0.1% TFA) 99%, RT=16.8 min. $^1$H NMR ($CDCl_3$) δ 0.95 (s, 9 H), 1.42–1.50 (m, 2H), 2.56–2.62 (m, 2H), 7.21–7.26 (m, 2H), 7.40–7.60 (m, 6H), 7.94 (d, 2H, J=7.8 Hz), 8.13–8.14 (m, 1H).

EXAMPLE 39

In vitro enzyme assay: human Branched Chain Amino Acid Aminotransferase cytosolic form (hBCATc) and mitochondrial form (hBCATm) as well as rat BCAT cytosolic form were assayed at 37° C. in 25 mM phosphate buffer pH 7.8. In addition, 2 mM DTT and 12.5 mM EDTA were added to the assay mixture. A coupling enzyme assay was used to monitor the production of glutamate. The formation of NADH from NAD+ at 340 nM was followed on a 96-well plate Molecular Devices plate reader. The following components were used in this coupled assay: 4 mM ADP, 1 mM NAD+, 750 μM L-Leucine, 500 μM a-ketoglutarate, 10 μM pyridoxal phosphate, 1 unit glutamate dehydrogenase, and 1.25 μg of the appropriate BCAT enzyme. Inhibitions by compounds were assayed by adding various concentrations to this coupled assay procedure as a DMSO stock up to a 5% v/v DMSO/buffer ratio. Data is shown in Table 1.

Enzyme Preparation: humanBCATc and ratBCATc were expressed in BL21(DE3) cells. A growing culture of cells was induced with 1 mM IPTG at room temperature overnight. These cells were harvested by centrifugation at 10,000 g for 20 minutes. The supernatant was discarded, and the cells were stored at −80° C. until needed. The protein was purified by the following method. The cell paste was resuspended in extraction buffer (0.1 M phosphate, pH 8.0, with 0.01 M Tris-HCL and 5 mM TCEP and then lysed on a French Press at 1000 psi. The lysate was centrifuged at 10,000 g for 15 minutes, and the pellet was discarded. The supernatant was loaded onto a Hitrap Chelating column previously charged with 0.1 M $NiSO_4$ and washed with 3 to 4 column volumes of extraction buffer. The column was then washed with 0.01 Tris, pH 7.5, 10% glycerol, 150 mM NaCl, 5 mM TCEP for two column volumes. The column was then further washed with two column volumes of 0.1 M phosphate, pH 6.0, 0.01 M Tris, 10% glycerol, and 750 mM NaCl. Finally, the column was washed with two column volumes of the same buffer plus 50 mM imidazole. The BCAT enzyme was then eluted with the same buffer but with 350 mM imidazole. The eluant was then dialyzed overnight against 10 mM phosphate buffer pH 8.0, 10% glycerol, and 5 mM TCEP. The dialyzed protein was then loaded onto a Q-sepharose column and eluted using a salt gradient. Active fractions were collected and further purified on a Superose-12 column to yield pure BCAT protein.

TABLE 1

| | In vitro Data | |
|---|---|---|
| Example No. | rrBCATc (μM) | rhBCATc (μM) |
| 1 | | 40 |
| 2 | 28.1 | 60 |
| 3 | | 0.7 |
| 4 | | 6 |
| 5 | | 10 |
| 6 | | 3 |
| 7 | | |
| 8 | | 7 |
| 9 | | 3.8 |
| 10 | | 13 |
| 11 | | 7.5 |
| 12 | | 4.6 |
| 13 | | |
| 14 | | 4.8 |
| 15 | | 4.9 |
| 16 | 4.4 | 27 |
| 17 | | 2.3 |
| 18 | 1.2 | 9.5 |
| 19 | 2.8 | 28 |
| 20 | 5.9 | 35 |
| 21 | 2.9 | 28 |
| 22 | | 110 |
| 23 | 0.43 | 17 |
| 24 | 1.2 | 57 |
| 25 | 1.5 | 16 |
| 26 | 2.2 | 34 |
| 27 | | 50 |
| 28 | 1.5 | 37 |
| 29 | 48 | 26 |
| 30 | | 2.8 |
| 31 | | |
| 32 | 1.3 | 27.6 |
| 33 | 0.25 | 14.3 |
| 34 | | 32.3 |
| 35 | 2.2 | 43.5 |
| 36 | 0.25 | 15.4 |
| 37 | 4.3 | 34.8 |
| 38 | 0.25 | 9.5 |

What is claimed is:
1. A compound of the Formula I

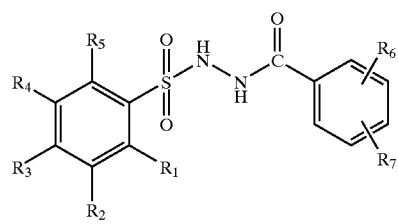

wherein:
R$_3$ is H, halogen, alkyl, carboxy, alkoxy, or substituted alkoxy;
R$_1$, R$_2$, R$_4$, and R$_5$ are independently, H, alkyl, substituted alkyl, alkoxy, substituted alkoxy, $NO_2$, halogen, or $CF_2$;
R$_6$ or R$_7$ is independently H, halogen, alkyl, substituted alkyl, arylalkyl, substituted arylalkyl, $(CH_2)_n$—$NHSO_2$-aryl, $(CH_2)_n$—$NHSO_2$-substituted aryl, $(CH_2)_n$—$NHSO_2$-alkyl, $(CH_2)_n$—$NHSO_2$-substituted alkyl, $(CH_2)_n$—$NHSO_2$-arylalkyl, $(CH_2)_n$—$NHSO_2$-substituted arylalkyl, $(CH_2)_n$aryl, $(CH_2)_n$-substituted aryl, $(CH_2)_n$-alkyl, $(CH_2)_n$-substituted alkyl, O-aryl, O-substituted aryl, O-alkyl, O-substituted alkyl O-arylalkyl, O-substituted arylalkyl, $(CH_2)_n$—$SO_2NH$-aryl, $(CH_2)_n$—$SO_2NH$-substituted aryl, $(CH_2)_n$—

SO₂NH-alkyl, (CH₂)ₙ—SO₂NH-substituted alkyl, (CH₂)ₙ—C(O)NH-arylalkyl, (CH₂)ₙ—C(O)NH-substituted arylalkyl, (CH₂)ₙ—C(O)NH-aryl, (CH₂)ₙ—C(O)NH-substituted aryl, (CH₂)ₙ—C(O)NH-alkyl, (CH₂)ₙ—C(O)NH-substituted alkyl, (CH₂)ₙ—SO₂NH-arylalkyl, (CH₂)ₙ—SO₂NH-substituted arylalkyl, (CH₂)ₙ—NH₂, (CH₂)ₙNH-aryl, (CH₂)ₙ—NH-substituted aryl, (CH₂)ₙ—NH-alkyl, (CH₂)ₙ—NH-substituted alkyl, (CH₂)ₙ—NH-arylalkyl, (CH₂)ₙ—NH-substituted arylalkyl, (CH₂)ₙ—NHSO₂-aryl, (CH₂)ₙ—NHSO₂-substituted aryl, (CH₂)ₙ—NHSO₂-alkyl, (CH₂)ₙ—NHSO₂-substituted alkyl, (CH₂)ₙ—NHC(O)-arylalkyl, (CH₂)ₙ—NHC(O)-substituted arylalkyl, (C≡C)-alkyl, (C≡C)-substituted alkyl, (C≡C)-arylalkyl, (C≡C)-substituted arylalkyl, (C≡C)-aryl, or (C≡C)-substituted aryl; and n is 0, 1, 2, or 3.

or a pharmaceutically acceptable salt, ester, prodrug or amide thereof, with the proviso that at least one of R₆ bar R₇ is O-aryl, O-substituted aryl, O-alkylaryl, or O-substituted alkaryl.

2. A compound according to claim 1 wherein the compound is:

4-Phenoxybenzoic acid, 2-[(3-methyl)phenylsulfonyl] hydrazide;
4-Phenoxybenzoic acid, 2-[3-bromophenylsulfonyl] hydrazide;
4-Phenoxybenzoic acid, 2-[2-chlorophenylsulfonyl] hydrazide;
4-Phenoxybenzoic acid, 2-[2-(trifluoromethoxy) phenylsulfonyl]hydrazide;
4-Phenoxybenzoic acid, 2-[(4methyl-3-nitro) phenylsulfonyl]hydrazide;
4-Phenoxybenzoic acid, 2-[2-trifluorophenylsulfonyl] hydrazide;
3-Phenoxybenzoic acid, 2-(phenylsulfonyl)hydrazide;
2-Phenoxybenzoic acid, 2-(phenylsulfonyl)hydrazide;
4-Phenoxybenzoic acid, 2-(phenylsulfonyl)hydrazide; and
4-Benzyloxybenzoic acid, 2-(phenylsulfonyl)hydrazide.

3. A pharmaceutical composition comprising a compound of claim 1 and pharmaceutically acceptable carrier.

4. A method of treating or preventing neuronal loss associated with stroke, ischemia, CNS trauma, hypoglycemia or surgery, or treating a neurodegenerative disease, or treating or preventing the adverse consequences of the overstimulation of the excitatory amino acids, or treating anxiety, psychosis, glaucoma, CMV retinitis, diabetic retinopathy, urinary incontinence, migraine headache, convulsions, aminoglycoside antibiotics-induced hearing loss, Parkinson's disease, chronic pain, neuropathic pain, or inducing anesthesia, opioid tolerance or withdrawal, or enhancing cognition, comprising administering to a patient in need of such treatment an effective amount of a compound of claim 1.

5. A method for inhibiting branched chain amino acid-dependent aninotransferase in a patient, the method comprising the step of administering to the patient a therapeutically effective amount of a compound of claim 1.

6. A method of treating or preventing neuronal loss associated with stroke, ischemia, CNS trauma, hypoglycemia or surgery, or treating a neurodegenerative disease, or treating or preventing the adverse consequences of the overstimulation of the excitatory amino acids, or treating anxiety, psychosis, glaucoma, CMV retinitis, diabetic retinopathy, urinary incontinence, migraine headache, convulsions, aminoglycoside antibiotics-induced hearing loss, Parkinson's disease, chronic pain, neuropathic pain, or inducing anesthesia, opioid tolerance or withdrawal, or enhancing cognition, comprising administering to a patient in need of such treatment an effective amount of a compound selected from the group consisting of Benzoic acid, 4-[[(2,4,6-trichlorophenyl)sulfonyl]amino]-, 2-(phenylsulfonyl)hydrazide;
Benzoic acid, 4-[[[4-(trifluoromethyl)phenyl]sulfonyl] amino]-, 2-(phenylsulfonyl)hydrazide;
Benzoic acid, 4-[[(3,4dimethoxyphenyl)sulfonyl]amino]-, 2-(phenylsulfonyl)hydrazide;
Benzoic acid, 4-[[[(4phenoxy)benzene]sulfonyl]amino]-, 2-(phenylsulfonyl)hydrazide;
Benzoic acid, 4-[[(2-chloro-6-methylphenyl)sulfonyl] amino]-, 2-(phenylsulfonyl)hydrazide;
Benzoic acid, 4-[(methylsulfonyl)amino]-, 2-(phenylsulfonyl)hydrazide;
Benzoic acid, 4-[[(4-methylphenyl)sulfonyl]amino]-, 2-(phenylsulfonyl)hydrazide;
Benzoic acid, 4-[[(4-ethylphenyl)sulfonyl]amino]-, 2-(phenylsulfonyl)hydrazide;
Benzoic acid, 4-[[(4-n-propylphenyl)sulfonyl]amino]-, 2-(phenylsulfonyl)hydrazide;
Benzoic acid, 4-[[(4-n-butylphenyl)sulfonyl]amino]-, 2-(phenylsulfonyl)hydrazide;
Benzoic acid, 4-[[(4-n-pentylphenyl)sulfonyl]amino]-, 2-(phenylsulfonyl)hydrazide;
Benzoic acid, 4-[[(4-fluorophenyl)sulfonyl]amino]-, 2-(phenylsulfonyl)hydrazide;
Benzoic acid, 4-[phenylsulfonyl]amino]-, 2-phenylsulfonyl) hydrazide;
4-Benzylamino-benzoic acid 2-(phenylsulfonyl)hydrazide;
Benzoic acid, 4-[[(3-methylphenyl)sulfonyl]amino]-, 2-(phenylsulfonyl)hydrazide;
4-Phenoxybenzoic acid, 2-[(3-methyl)phenylsulfonyl] hydrazide;
4-Phenoxybenzoic acid, 2-[3-bromophenylsulfonyl] hydrazide;
4-Phenoxybenzoic acid, 2-[2chlorophenylsulfonyl] hydrazide;
4-Phenoxybenzoic acid, 2-[2-trifluoromethoxy) phenylsulfonyl]hydrazide;
4-Phenoxybenzoic acid, 2-[(4-methyl-3-nitro) phenylsulfonyl]hydrazide;
4-Phenoxybenzoic acid, 2-[2-trifluorophenylsulfonyl] hydrazide;
4-(1,1-Dimethylethyl)-benzoic acid 2-(phenylsulfonyl) hydrazide;
[1,1'-Biphenyl]-4-carboxylic acid 2-(phenylsulfonyl) hydrazide;
3-Phenoxybenzoic acid, 2-(phenylsulfonyl)hydrazide;
2-Phenoxybenzoic acid, 2-(phenylsulfonyl)hydrazide;
4-Phenoxybenzoic acid, 2-(phenylsulfonyl)hydrazide;
4-Benzyloxybenzoic acid, 2-(phenylsulfonyl)hydrazide;
Benzoic acid, 4-[[(4-methoxyphenyl)sulfonyl]amino]-, 2-(phenylsulfonyl)hydrazide;
4-Iodo-benzoic acid, 2-(phenylsulfonyl)hydrazide;
4-Phenacetylenyl-benzoic acid, 2-(phenylsulfonyl) hydrazide;
Phenethyl-benzoic acid, 2-(phenylsulfonyl)hydrazide;
4-(3-Cyclohexyl-1-propynyl)-benzoic acid, 2-(phenylsulfonyl)hydrazide;
4-(3-Cyclohexyl-3-hydroxy-1-propynyl)-benzoic acid, 2-(phenylsulfonyl)hydrazide;
4-(3-Cyclohexyl-3-hydroxy-1-propyl)benzoic acid, 2phenylsulfonyl)hydrazide;

4-(3,3-Dimethyl-1-butynyl)-benzoic acid, 2-(phenylsulfonyl)hydrazide; and
4-(3,3-Dimethyl-1-butyl)-benzoic acid, 2-(phenylsulfonyl)hydrazide.

7. A method for inhibiting branched chain amino acid-dependent aminotransverase in a patient, the method comprising the step of administering to the patient a therapeutic effective amount of a compound selected from the group consisting of Benzoic acid, 4-amino-2-(phenylsulfonyl)hydrazide;
Benzoic acid, 4-[[(2,4,6-trichlorophenyl)sulfonyl]amino]-, 2-(phenylsulfonyl)hydrazide;
Benzoic acid, 4-[[[4-(trifluoromethyl)phenyl)sulfonyl]amino]-, 2-(phenylsulfonyl)hydrazide;
Benzoic acid, 4-[[(3,4-dimethoxyphenyl)sulfonyl]amino]-, 2-(phenylsulfonyl)hydrazide;
Benzoic acid, 4-[[[(4phenoxy)benzene]sulfonyl]amino]-, 2-(phenylsulfonyl)hydrazide;
Benzoic acid, 4-[[(2-chloro-6-methylphenyl)sulfonyl]amino]-, 2-(phenylsulfonyl)hydrazide;
Benzoic acid, 4-[(methylsulfonyl)amino]-, 2-(phenylsulfonyl)hydrazide;
Benzoic acid, 4-[[(4-methylphenyl)sulfonyl]amino]-, 2-(phenylsulfonyl)hydrazide;
Benzoic acid, 4-[[4-ethylphenyl)sulfonyl]amino]-, 2-(phenylsulfonyl)hydrazide;
Benzoic acid, 4-[[(4-n-propylphenyl)sulfonyl]amino]-, 2-(phenylsulfonyl)hydrazide;
Benzoic acid, 4-[[(4-n-butylphenyl)sulfonyl]amino]-, 2-(phenylsulfonyl)hydrazide;
Benzoic acid, 4-[[((4-n-pentylphenyl)sulfonyl]amino]-, 2-(phenylsulfonyl)hydrazide;
Benzoic acid, [[(4-fluorophenyl)sulfonyl]amino]-, 2-(phenylsulfonyl)hydrazide,
Benzoic acid, 4-[phenylsulfonyl]amino]-, 2-(phenylsulfonyl)hydrazide;
4-Benzylamino-benzoic acid 2-(phenylsulfonyl)hydrazide;
Benzoic acid, 4-[[(3-methylphenyl)sulfonyl]amino]-, 2-(phenylsulfonyl)hydrazide;
4-Phenoxybenzoic acid, 2-[(3-methyl)phenylsulfonyl]hydrazide;
4-Phenoxybenzoic acid, 2-[3-bromophenylsulfonyl]hydrazide;
4-Phenoxybenzoic acid, 2-[2-chlorophenylsulfonyl]hydrazide;
4-Phenoxybenzoic acid, 2-[2-trifluoromethoxy)phenylsulfonyl]hydrazide;
4-Phenoxybenzoic acid, 2-[(4-methyl-3-nitro)phenylsulfonyl]hydrazide;
4-Phenoxybenzoic acid, 2-[2-trifluorophenylsulfonyl]hydrazide;
4-(1,1-Dimethylethyl)-benzoic acid 2-(phenylsulfonyl)hydrazide;
[1,1'-Biphenyl]-4-carboxylic acid 2-(phenylsulfonyl)hydrazide;
3-Phenoxybenzoic acid, 2-(phenylsulfonyl)hydrazide;
2-Phenoxybenzoic acid, 2-(phenylsulfonyl)hydrazide;
4-Phenoxybenzoic acid, 2-(phenylsulfonyl)hydrazide;
4-Benzyloxybenzoic acid, 2-(phenylsulfonyl)hydrazide;
Benzoic acid, 4-[[4-methoxyphenyl)sulfonyl]amino]-, 2-(phenylsulfonyl)hydrazide;
4-Iodo-benzoic acid, 2-(phenylsulfonyl)hydrazide;
4-Phenacetylenyl-benzoic acid, 2-(phenylsulfonyl)hydrazide;
Phenethyl-benzoic acid, 2-(phenylsulfonyl)hydrazide;
4-(3-Cyclohexyl-1-propynyl)-benzoic acid, 2-phenylsulfonyl)hydrazide;
4-(3Cyclohexyl-3-hydroxy-1-propynyl)-benzoic acid, 2-(phenylsulfonyl)hydrazide;
4-(3-Cyclohexyl-3-hydroxy-1-propyl)-benzoic acid, 2-(phenylsulfonyl)hydrazide;
4-(3,3-Dimethyl-1-butynyl)-benzoic acid, 2-(phenylsulfonyl)hydrazide; and
4-(3,3-Dimethyl-1-butynyl)-benzoic acid, 2-(phenylsulfonyl)hydrazide.

\* \* \* \* \*